(12) United States Patent
Khalid

(10) Patent No.: US 10,383,794 B2
(45) Date of Patent: Aug. 20, 2019

(54) MEDICATION COMPLIANCE ALERT DEVICE

(71) Applicant: NexPil, Inc., Niles, IL (US)

(72) Inventor: Syed Khalid, Niles, IL (US)

(73) Assignee: NexPil, Inc., Niles, IL (US)

( * ) Notice: Subject to any disclaimer, the term of this patent is extended or adjusted under 35 U.S.C. 154(b) by 0 days.

(21) Appl. No.: 15/997,820

(22) Filed: Jun. 5, 2018

(65) Prior Publication Data

US 2018/0280245 A1 Oct. 4, 2018

Related U.S. Application Data

(63) Continuation-in-part of application No. 15/958,855, filed on Apr. 20, 2018, now abandoned, which is a
(Continued)

(51) Int. Cl.
*A61J 7/04* (2006.01)
*G08B 21/24* (2006.01)
(Continued)

(52) U.S. Cl.
CPC .......... *A61J 7/0418* (2015.05); *A61J 7/0084* (2013.01); *A61J 7/04* (2013.01); *A61J 7/0409* (2013.01);
(Continued)

(58) Field of Classification Search
CPC combination set(s) only.
See application file for complete search history.

(56) References Cited

U.S. PATENT DOCUMENTS 7,715,277 B2 * 5/2010 de la Huerga ........ A61J 7/0084
368/10
9,474,695 B1 * 10/2016 Khalid ................. A61J 7/0409
(Continued)

OTHER PUBLICATIONS

U.S. Appl. No. 14/521,379, "Non-Final Office Action," dated Dec. 21, 2015, 11 pages.
(Continued)

*Primary Examiner* — Travis R Hunnings
(74) *Attorney, Agent, or Firm* — McDonnell Boehnen Hulbert & Berghoff LLP

(57) ABSTRACT

Example embodiments relate to medication compliance alert devices. An example embodiment includes a method. The method includes capturing information about a medication label associated with a medication. The method also includes analyzing, by a first computing device, the information about the medication label to extract medication information. Further, the method includes generating, by the first computing device, a medication schedule for a corresponding patient associated with the medication. The medication schedule includes a dosage strength and dosage frequency. In addition, the method includes prompting, by a second computing device, the corresponding patient to take an amount of the medication corresponding to the dosage strength at a predetermined time according to the medication schedule. Still further, the method includes receiving, by the second computing device, an indication that the corresponding patient has taken the amount of the medication corresponding to the dosage strength.

31 Claims, 18 Drawing Sheets

Related U.S. Application Data continuation of application No. 15/334,115, filed on Oct. 25, 2016, now Pat. No. 9,949,895, which is a continuation of application No. 14/521,379, filed on Oct. 22, 2014, now Pat. No. 9,474,695.

(60) Provisional application No. 61/894,737, filed on Oct. 23, 2013.

(51) Int. Cl.
*A61J 7/00* (2006.01)
*G16H 20/10* (2018.01)
*A61J 1/14* (2006.01)

(52) U.S. Cl.
CPC .......... *A61J 7/0436* (2015.05); *A61J 7/0454* (2015.05); *A61J 7/0472* (2013.01); *A61J 7/0481* (2013.01); *G08B 21/24* (2013.01); *G16H 20/10* (2018.01); *A61J 1/1412* (2013.01); *A61J 2200/30* (2013.01); *A61J 2205/10* (2013.01); *A61J 2205/20* (2013.01); *A61J 2205/40* (2013.01); *A61J 2205/50* (2013.01); *A61J 2205/60* (2013.01); *A61J 2205/70* (2013.01)

(56) References Cited

U.S. PATENT DOCUMENTS

| | | | |
|---|---|---|---|
| 9,949,895 | B1 | 4/2018 | Khalid |
| 2007/0016443 | A1* | 1/2007 | Wachman ........... G06F 19/3456 705/2 |
| 2012/0038226 | A1* | 2/2012 | Tran ................... G06F 19/3462 307/116 |
| 2013/0002795 | A1* | 1/2013 | Shavelsky ................ A61J 7/04 348/14.01 |
| 2013/0030566 | A1* | 1/2013 | Shavelsky ................ A61J 7/04 700/244 |
| 2013/0197693 | A1* | 8/2013 | Kamen ............... G06F 19/3418 700/244 |
| 2015/0283036 | A1* | 10/2015 | Aggarwal ................ A61J 7/04 206/534 |
| 2017/0283151 | A1 | 10/2017 | Stormer et al. |

OTHER PUBLICATIONS

U.S. Appl. No. 14/521,379, "Notice of Allowance," dated Jun. 23, 2016, 5 pages.
U.S. Appl. No. 15/334,115, "Non-Final Office Action," dated Aug. 9, 2017, 6 pages.
U.S. Appl. No. 15/334,115, "Notice of Allowance," dated Dec. 13, 2017, 5 pages.

\* cited by examiner

MEDICATION COMPLIANCE ALERT DEVICE

CROSS-REFERENCE TO RELATED APPLICATIONS

This application is a Continuation-in-Part of U.S. application Ser. No. 15/958,855, filed Apr. 20, 2018; which is a Continuation of U.S. application Ser. No. 15/334,115, filed Oct. 25, 2016, that resulted in U.S. Pat. No. 9,949,895, issued on Apr. 24, 2018; which is a Continuation of U.S. application Ser. No. 14/521,379, filed Oct. 22, 2014, that resulted in U.S. Pat. No. 9,474,695, issued on Oct. 25, 2016; which claims the benefit of U.S. Provisional Application No. 61/894,737, filed Oct. 23, 2013; the contents of each of which are incorporated herein by reference in their entirety.

BACKGROUND

Every day, significant numbers of patients fail to take their medication as directed. Such non-compliance with prescription regimens can result in reduced efficacy of treatments, increased hospitalizations, and even death. Various approaches for promoting compliance have been developed, yet these approaches can fail in several ways.

For example, day-of-the-week or other pillbox organizers frequently require a user to transfer pills from an original container from a pharmacy into alternate containers that will be utilized to help the user remember when to take the pills. This process may introduce opportunities for error. Additionally, the extra burden of this process may become a potential promoter of non-compliance, especially for patients that lack the discipline or mental faculties to consistently complete the sorting and replenishing tasks.

With alarm or notification reminder systems, a patient who is not able to hear or see the notification will simply not be reminded, resulting in inadvertent non-compliance. Furthermore, alarms such as on wristwatches or phone applications may be easily turned off without actually prompting the patient to take the medication.

SUMMARY

The specification and drawings disclose embodiments that relate to medication compliance alert devices.

A device can include an alert mechanism and a detection mechanism. The alert mechanism can activate an alert for a user to take a medication from a target medication receptacle. The detection mechanism can detect a tag associated with a medication receptacle. Actions may be performed based on a correlation between the detected tag and the target medication receptacle, such as deactivating the alert based at least in part on detecting the tag associated with the target medication receptacle.

In a first aspect, the disclosure describes a method. The method includes capturing information about a medication label associated with a medication. The method also includes analyzing, by a first computing device, the information about the medication label to extract medication information. Further, the method includes generating, by the first computing device, a medication schedule for a corresponding patient associated with the medication. The medication schedule includes a dosage strength and dosage frequency. In addition, the method includes prompting, by a second computing device, the corresponding patient to take an amount of the medication corresponding to the dosage strength at a predetermined time according to the medication schedule. Still further, the method includes receiving, by the second computing device, an indication that the corresponding patient has taken the amount of the medication corresponding to the dosage strength.

In a second aspect, the disclosure describes a mobile computing device. The mobile computing device is configured to capture information about a medication label associated with a medication. The mobile computing device is also configured to analyze the information about the medication label to extract medication information. Further, the mobile computing device is configured to generate a medication schedule for a corresponding patient associated with the medication. The medication schedule includes a dosage strength and a dosage frequency. In addition, the mobile computing device is configured to prompt the corresponding patient to take an amount of the medication corresponding to the dosage strength at a predetermined time according to the medication schedule. Still further, the mobile computing device is configured to receive an indication that the corresponding patient has taken the amount of the medication corresponding to the dosage strength.

In a third aspect, the disclosure describes a non-transitory, computer-readable medium having instructions stored thereon that, when executed by a processor, perform a method. The method includes receiving information, from a computing device, about a medication label associated with a medication. The method also includes analyzing the information about the medication label to extract medication information. Further, the method includes generating a medication schedule for a corresponding patient associated with the medication. The medication schedule includes a dosage strength and a dosage frequency. In addition, the method includes transmitting, to the computing device, the medication schedule for the corresponding patient. Still further, the method includes receiving, from the computing device, an indication that the corresponding patient has taken an amount of the medication corresponding to the dosage strength. The indication that the corresponding patient has taken the amount of the medication corresponding to the dosage strength was received by the computing device in response to the computing device prompting the corresponding patient to take the amount of the medication corresponding to the dosage strength at a predetermined time according to the medication schedule.

The foregoing summary is illustrative only and is not intended to be in any way limiting. In addition to the illustrative aspects, embodiments, and features described above, further aspects, embodiments, and features will become apparent by reference to the figures and the following detailed description.

DETAILED DESCRIPTION OF THE INVENTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Embodiments disclosed herein are directed to medication compliance systems that include medication alert devices. A medication alert device can provide a reminder to a patient to take a medication. The medication alert device may indicate a medication receptacle (such as a pill bottle) that may contain the medication referenced in the reminder, such as by showing a shape and/or color indicia associated with the medication receptacle. The patient can select a medication receptacle and bring a cap or other feature of the medication receptacle near the medication alert device. The medication alert device can detect that the feature is nearby and determine which medication receptacle is detected. Based on the medication receptacle detected, the medication alert device can perform a variety of actions. For example, when the detected medication receptacle matches the medication referenced in the reminder, the medication alert device may provide a confirmation of the match. In a further example, detection of a medication receptacle may indicate that the patient has taken a dose of the medication associated with the receptacle, and the medication alert device may deactivate a reminder, such as turning off a shape and/or color indicia. In another example, a number of times that a receptacle has been detected may be used to estimate an amount of medication consumed or remaining for a particular receptacle. In yet another example, an amount of time between a reminder and a detection may be used to determine patterns of behavior and/or adjust timing of future reminders. In various embodiments, the medication alert device can communicate with other devices, such as to provide information about medication compliance to healthcare providers and/or to receive updates, such as changes to reminder schedules or organization of medication receptacles.

Figure 1:
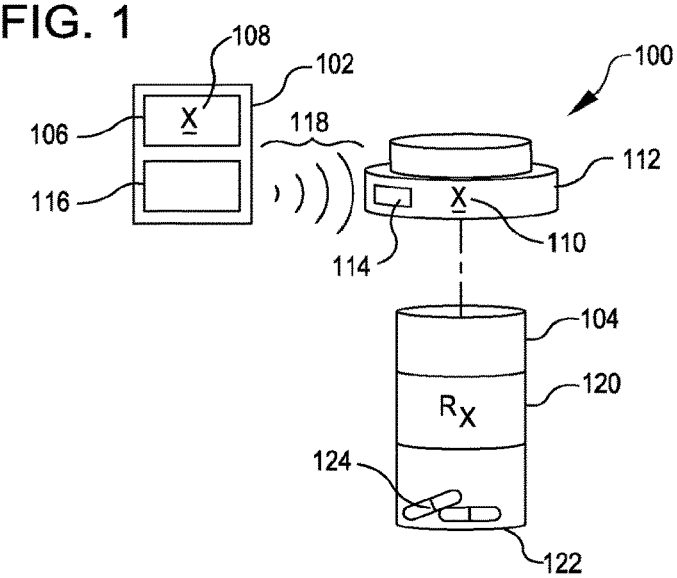
FIG. 1 is a schematic diagram showing an example of a medication compliance system in accordance with at least one embodiment.

Referring now to the drawings, in which like reference numerals represent like parts throughout the several views, FIG. 1 shows an example of a medication compliance system 100. The medication compliance system 100 can include a medication alert device 102 and a medication receptacle 104.

The medication receptacle 104 may be a pill bottle or any other receptacle capable of containing medication 124. Although description herein primarily references pills, the disclosure is equally applicable to medication 124 of any kind, including, but not limited to, creams, ointments, syrups, serums, comestibles, or injectionables. The medication receptacle 104 may include a cap 112 that is removable to access medication 124 contained within a body 122 of the medication receptacle 104. The medication receptacle 104 may include a label 120 that identifies the medication intended to be contained in the medication receptacle 104.

The medication alert device 102 can come in a variety of forms. In some embodiments, the device is wearable by a user of the device. For example, the device may be incorporated into a wristband, a watch, a bracelet, a necklace, a ring, a garment, a headband, a belt, a pair of suspenders, a pair of glasses, a glove, a gauntlet, a girdle, a harness, a shoe, or an implantable device. In some embodiments, the device may be sized to facilitate ease of transport, such as to fit in a user's pocket or purse. For example, the device may be incorporated into a card, a keychain, a fob, a pocketknife, or a coin. In some embodiments, the device may include a software component of another device, such as a personal computer, a tablet computer, a cell phone, or a smart watch. The device can be powered by any suitable mechanism including, but not limited to, batteries, solar power, kinetic power, powered derived from thermal couples, and/or power obtained by vibration.

The medication alert device 102 can include an alert mechanism 106 and a detection mechanism 116. The alert mechanism 106 and the detection mechanism 116 can be collocated in a single device, or provided over two devices. The alert mechanism 106 can provide a reminder to a patient to take a medication 124. For example, the alert mechanism 106 can provide a reminder at a particular time of the day at which the medication 124 is to be taken or after a certain interval since the medication 124 was last taken.

In some embodiments, the alert mechanism 106 can provide a visual notification, such as to provide a visual reminder to take the medication 124. The visual notification may include a display of an indicia 108 that matches an indicia 110 on the cap 112 or other feature of the medication receptacle 104, such as the label 120 or body 122. Examples of the indicia 108,110 include shapes, colors, and/or symbols (which can include text strings of letters or words). Matching indicia 108 and 110 may assist a patient in locating a medication receptacle 104 for the medication 124 that is the subject of the reminder. In an illustrative example, the alert mechanism 106 may include a light-emitting diode (LED) or a display capable of producing a wide range of different colors that correspond to a given color on some part of the medication receptacle 104. In some embodiments, a display may be included separately from the alert mechanism and/or may display other information in addition to, or instead of, a reminder to take a medication 124. As an illustrative example, the medication alert device 102 may include a touchscreen display user interface through which a user may configure the medication alert device 102 and/or receive other information, such as information about the medication 124 and/or other healthcare details for the user.

In some embodiments, the alert mechanism 106 can provide an audible notification. For example, the alert mechanism may include a speaker capable of making a sound to remind a patient to take medication 124. The speaker may be tunable to cater to users with auditory impairment, such as altering a frequency of the audible notification for individuals with a narrower range of audible tones and/or increasing a volume of the audible notification for those with difficulties hearing lower volume sounds. Illustrative examples of audible notifications include beeps, tones, speech, and/or music. The alert mechanism 106 may be programmable to allow a user to record and/or otherwise provide a customized audible notification.

In some embodiments, the alert mechanism 106 can provide a tactile notification. For example, the alert mechanism 106 can include a vibration system capable of vibrating a part or a whole of the medication alert device 102, such as to provide a physical stimulus if and when the device is worn by a user or in contact with the user. Any one of the notifications described herein (e.g., visible notifications, audible notifications or tactile notifications) can be used individually and/or in combination with other notifications or types of notifications. In some embodiments, a same type of notification can be provided in different manners to indicate different meanings. As an illustrative example, the alert mechanism 106 may cause the medication alert device 102 to provide vibrating pulses in pairs to indicate that a user should take two pills instead of one. In general, the medication alert device 102 may be configured to accommodate different varieties of medication regimens and/or dosage.

In embodiments, the device 10 utilizes near field communication as part of the detection mechanism 116. For example, the detection mechanism 116 may detect a radio-frequency identification (RFID) tag 114 or other item, such as a marker, that can be used for identification within a certain distance of the detection mechanism 116. As illustrative examples, the certain distance may include a distance that corresponds to an item having the tag 114 coming into contact with the device 10, coming within a distance threshold of the device (such as 1 mm), or being within a distance range from the device (such as between 0 mm and 20 mm). The tag 114 may be part of a cap 112, a label 120, a body 122, or other feature of the medication receptacle 104. Accordingly, the detection mechanism 116 can detect if the medication receptacle 104 is near the medication alert device 102. The detection mechanism 116 can detect such proximity in any suitable manner. For example, the detection mechanism 116 can wirelessly detect the tag 114, as at 118, using RFID or other wireless near field communication technology. Although wireless near field communication technology is one option, proximity may be detected using any suitable technology, including scanning bar codes, a plug-in/socket arrangement, and/or any other communication method between nearby objects.

In embodiments, the medication compliance system 100 provides a mechanism for tracking a user's consumption of medication 124. For example, each time the tag 114 is detected may correspond to another instance of the patient taking the medication 124.

In some embodiments, a reminder provided by the alert mechanism 106 may be persistent. As illustrative examples, a visible, flashing light notification may continue flashing until deactivated, or an audible notification may repeat at recurring intervals until deactivated. In some aspects, the notification may persist until a user has indicated that a medication 124 has been administered, such as by detection of a tag 114 associated with a medication receptacle 104 for the medication 124.

In some embodiments, the medication alert device 102 can execute other functions in addition to-or as an alternative to-deactivating a reminder in response to detecting a tag 114. Examples of some such functions are described in greater detail with respect to subsequent figures herein.

Figure 2:
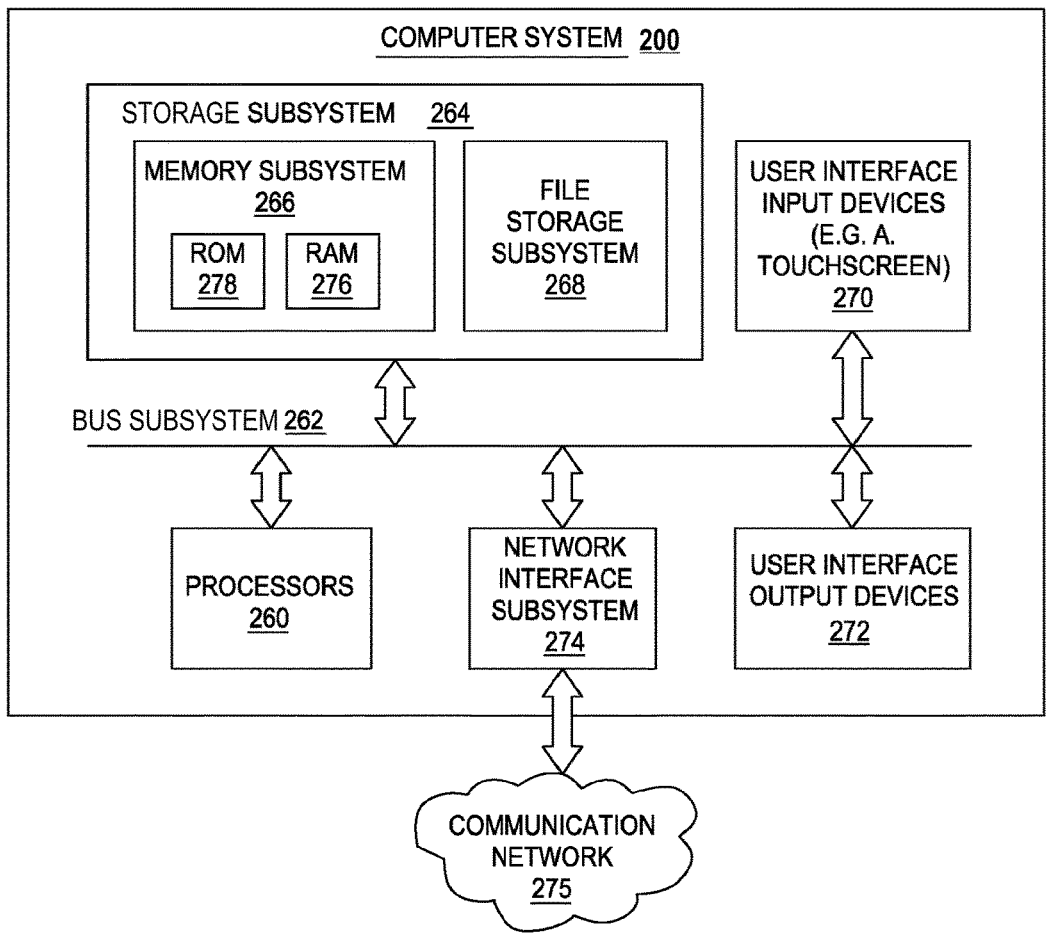
FIG. 2 is a simplified block diagram of an example computer system in accordance with at least one embodiment.

FIG. 2 is a simplified block diagram of an example computer 200 that can be used in accordance with embodiments described herein. The computer 200 typically includes at least one processor 260 which communicates with a number of peripheral devices via a bus subsystem 262. These peripheral devices may include a storage subsystem 264, comprising a memory subsystem 266 and a file storage subsystem 268, user interface input devices 270, user interface output devices 272, and a network interface subsystem 274. Network interface subsystem 274 provides an interface to a communication network 275 for communication with other systems, computers, databases, or the like.

The processor 260 performs the operation of the computer systems 200 using execution instructions stored in the memory subsystem 266 in conjunction with any data input from an operator. Such data can, for example, be input through user interface input devices 270, such as the graphical user interface. Thus, processor 260 can include an execution area into which execution instructions are loaded from memory. These execution instructions will then cause processor 260 to send commands to the computer system 200, which in turn control the operation of the container control electronics. Although described as a "processor" in this disclosure and throughout the claims, the functions of the processor may be performed by multiple processors in one computer or distributed over several computers.

User interface input devices 270 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. In general, use of the term "input device" is intended to include a variety of conventional and proprietary devices and ways to input information into the computer system. Such input devices will often be used to download a computer executable code from a computer network or a tangible storage media embodying steps or programming instructions for any of the methods of the present invention.

User interface output devices 272 may include a display subsystem, a printer, a fax machine, or non-visual displays such as audio output devices. The display subsystem may be a cathode ray tube (CRT), a flat-panel device such as a liquid-crystal display (LCD), a projection device, or the like. The display subsystem may also provide non-visual display such as via audio output devices. In general, use of the term "output device" is intended to include a variety of conventional and proprietary devices and ways to output information from the computer system to a user.

Storage subsystem 264 stores the basic programming and data constructs that provide the functionality of the various embodiments. For example, database and modules implementing the functionality of embodiments described herein may be stored in storage subsystem 264. These software modules are generally executed by processor 260. In a distributed environment, the software modules may be stored in a memory of a plurality of computer systems and executed by processors of the plurality of computer systems. Storage subsystem 264 typically comprises memory subsystem 266 and file storage subsystem 268.

Memory subsystem 266 typically includes a number of memories including a main random-access memory (RAM) 276 for storage of instructions and data during program execution and a read-only memory (ROM) 278 in which fixed instructions are stored. File storage subsystem 268 provides persistent (non-volatile) storage for program and data files, and may include a hard disk drive, re-writable non-volatile memory chips (such as Flash memory), a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to the computer system. The databases and modules implementing the functionality of the present invention may also be stored by file storage subsystem 268. The file storage subsystem may have directory and file descriptions for accessing the files, or it may store data without descriptions and rely on the databases and modules of the system to locate the data.

Bus subsystem 262 provides a mechanism for letting the various components and subsystems of the computer system communicate with each other as intended. The various subsystems and components of the computer system need not be at the same physical location but may be distributed at various locations within a distributed network. Although bus subsystem 262 is shown schematically as a single bus, alternate embodiments of the bus subsystem may utilize multiple busses.

The computer 200 itself can be of varying types including a personal computer, a portable computer, a workstation, a computer terminal, a network computer, a module in a circuit board, a mainframe, or any other data processing system. Due to the ever-changing nature of computers and networks, the description of the computer system depicted in FIG. 2 is intended only as a specific example for purposes of illustrating one embodiment. Many other configurations of the computer system are possible having more or less components than the computer system depicted in FIG. 2.

Figure 3:
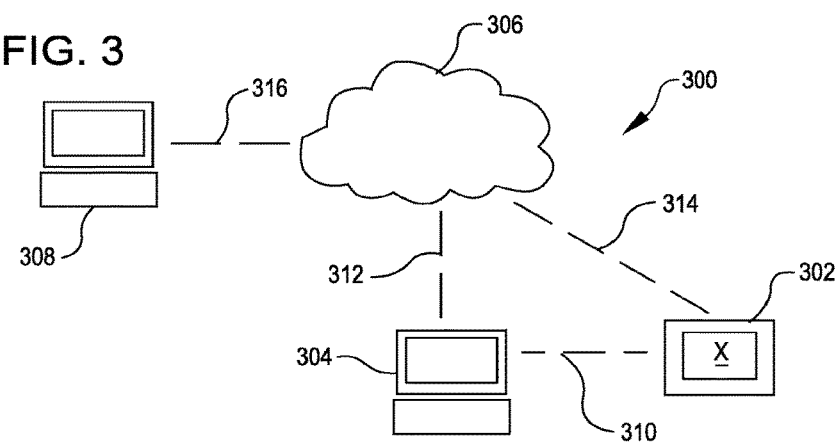
FIG. 3 is a schematic diagram depicting an illustrative system in which techniques herein may be implemented in accordance with at least one embodiment.

FIG. 3 is a schematic diagram depicting an illustrative system 300 in which techniques herein may be implemented in accordance with at least one embodiment. The system 300 can include a device 302 for medication alerts, such as the medication alert device 102 described above with respect to FIG. 1. The device 302 can include a computer (e.g., such as the computer 200 of FIG. 2) and/or the device 302 may communicate with a computer that is separate from the device 302, such as a user computer 304 or a third party computer 308. The user computer 304 may be a computer (e.g., such as the computer 200 of FIG. 2) operated by a user of the device 302. In some embodiments, the device 302 may include a mobile computing device, a tablet computing device, a wearable computing device, a laptop computing device, a desktop computing device, a computing device associated with a smart speaker, or a computing device embedded within a household appliance. The third party computer 308 can be a computer (e.g., such as the computer 200 of FIG. 2) operated by a healthcare provider, a pharmacy, a research institution, or any other party of relevance with respect to the user's utilization of the device 302. In various embodiments, the third party computer 308 may include a server computing device (e.g., a cloud server). In some embodiments, the third party computer 308 may store information regarding various patients in a relational database (e.g., a relational database executing structured query language (SQL)).

The device 302 may communicate, as at 310, with the user computer 304. Communication can include sending and/or receiving information. The user computer 304 can, in turn, communicate with third party computers 308, such as at 312 and 316 via a network 306, such as the communication network 275. In some aspects, the device 302 can communicate directly with a third party computer 308 via the network 306, as at 314 and 316. The device 302 may communicate by any suitable manner including, but not limited to, wired communication or wireless communication such as near field communication, Bluetooth, WiFi, cellular radio standards, or other wireless protocols. In some embodiments, the user computer 304 may include a mobile computing device, a tablet computing device, a wearable computing device, a laptop computing device, a desktop computing device, a computing device associated with a smart speaker, or a computing device embedded within a household appliance. In some embodiments, the device 302 and the user computer 304 may be integrated together into a single device.

Figure 4:
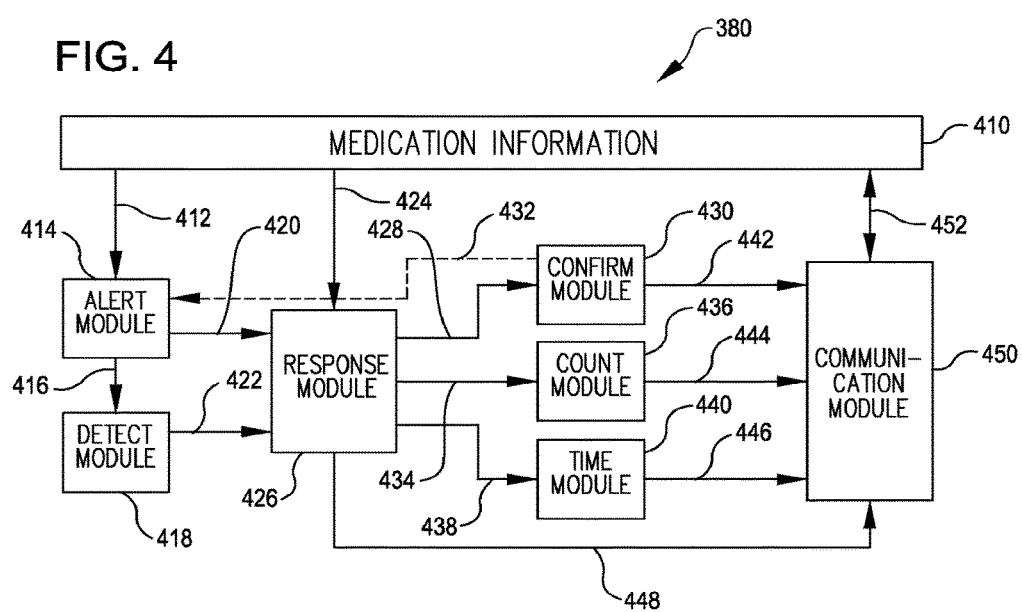
FIG. 4 schematically illustrates a plurality of modules that may carry out embodiments.

FIG. 4 schematically illustrates a plurality of modules 380 that may carry out embodiments. The modules 380 may be software modules, hardware modules, or a combination thereof If the modules are software modules, the modules will be embodied on a computer readable medium and processed by a processor 260 in any of computer systems of the present disclosure.

At least some of the modules 380 may utilize medication information 410. For example, the medication information 410 may be stored in a storage subsystem 264 of any one of the computers 200 described herein. The medication information 410 may include, but is not limited to, names of medications associated with a user of a medication alert device, dosage information for medications, indicia associated with medications, tags associated with medications, administration timing for medications, quantities of medication for a user to take (e.g., number of pills), number of refills a patient has on file with a pharmacy for medications, whether a doctor notification or supplemental prescription is required for additional refills of any medications, a patient's age, a patient's gender, conditions that a patient has been diagnosed with, an area in which the patient lives, a pharmacy that the patient uses, and/or information about the patient's healthcare providers.

An alert module 414 can utilize medication information 410, such as at 412. The alert module 414 can trigger reminders for a patient to take a medication. For example, the alert module 414 may control an alert mechanism 106 based on medication information 410, such as timing information or indicia associated with the medication.

A detect module 418 can control detection performed by a medication alert device. For example, the detect module 418 can operate a detection mechanism 116 of a medication alert device 102. The detect module 418 may activate the detection mechanism 116 in response to information received from the alert module, as at 416, such as that an alert has been activated. Such an arrangement may reduce a power consumption by the detection mechanism 116. The detect module 418 may determine which tag 114, if any, is in proximity to the medication alert device 102.

The response module 426 can determine a response to information received from the detect module 418 at 422, information received from the alert module 414 at 420, medication information 410 accessed at 424, or any combination thereof For example, the response module 426 may process and/or transfer information to other modules, such as at 428, 434, 438, and/or 448. The response module 426 may determine information to send to other modules, based on information received by the response module. For example, the response module may send information relating to one type of medication to one subset of modules and send information relating to a different medication to a different subset of modules.

A confirm module 430 can determine if a medication referenced in a reminder issued by the alert module is the same as the medication corresponding to a detection made by the detect module 418. For example, the confirm module 430 may receive information (e.g., at 428 from the response module 426) that an alert was activated to remind a patient to take aspirin from a first bottle and that the detect module 418 detected a tag for a bottle associated with aspirin. The confirm module 430 may provide a confirmation that the selected bottle corresponds to the medication of the reminder, in this case, aspirin. In some aspects, the confirm module 430 can communicate with the alert module 414 (e.g., at 432), such as to deactivate a reminder as a way of providing a confirmation that the medication of the detected bottle and the medication of the reminder match. In another illustrative example, the confirm module 430 may receive an indication that an alert was sent to remind a patient to take ibuprofen and a subsequent detection was associated with a bottle for aspirin. The confirm module 430 may provide a warning that the medication of the reminder and the medication of the detected bottle do not match.

A count module 436 can generate information based on a number of times detections have been made. For example, the count module 436 can receive information, as at 434, about the number of times a tag 114 for a particular medication receptacle 104 has been detected. The count module 436 may determine an amount of medication 124 remaining in a particular medication receptacle 104 by subtracting a number of times an associated tag 114 has been detected from an initial amount of the medication 124 determined from the medication information 410.

A time module 440 can determine timing information associated with other operations described herein. For example, the time module may receive, as at 438, information about when an alert was triggered and when a matching detection was made. The time difference may be used to analyze and/or adjust the timing of future reminders and/or other actions.

A communication module 450 can coordinate communication between modules 380 and/or other components described herein. To this end, the communication module may receive information from the confirm module 430, as at 442, the count module 436, as at 444, the time module 440, as at 446, the response module 426, as at 448, medication information 410, as at 452, or any combination thereof In an illustrative example, the response module 426 can determine that count information from the count module 436 should be communicated from the device 302 by the communication module 450 to another device, such as a user computer 304 and/or a third party computer 308. More specifically, medication information 410 may indicate that a particular medication receptacle 104 includes three pills, the detect module 418 may detect that the medication receptacle 104 was brought into proximity with the medication alert device 102, the response module 426 may forward the information to the count module 436, the count module 436 may calculate that two pills remain in the medication receptacle 104 based on the detection and previous count, the response module 426 may cause the information to be communicated via the communication module 450 to update the medication information 410 with the new count of two pills, and the response module 426 may cause information to be communicated via the communication module 450 to a third party computer 308 of a pharmacy to automatically request a refill of the medication.

Medication alert devices such as described herein (e.g., device 302) can include additional functionality which may be facilitated by the communication module 450 communicating between the device 302 and other electronic devices, such as computers 200. For example, information associated with the device 302 may be conveyed as electronic messages in the form of email, social networking sites, conventional mail, phone calls, voicemail messages, messaging services, text messaging, short message service, and/or multimedia messaging service. Such information may be provided to a user, a healthcare provider, pharmacy, an insurance provider, a research institution, other parties, and/or any combination thereof For example, electronic messages may be utilized to: remind a user to request a refill, request a new prescription, and/or pick up a completed prescription; notify a user that a prescription has been filled at a pharmacy, that new alternative drugs are available, that follow-up appointments with healthcare providers are needed or scheduled, that test results are available, the costs associated with further prescriptions or appointments; inform a user about relevant and contextual information based upon weather and/or environmental conditions (e.g., if a patient has a respiratory condition, there is a smog alert in the area); and/or facilitate communication between the physician, user, pharmacy, insurance provider, research institute, and/or other parties.

In some aspects, the communication module 450 can facilitate communication between the device and other sensors and/or medical devices. Such communication may permit data about the patient's physiological conditions to be correlated with the patient's medication consumption history, permit detected physiological conditions of the patient to determine adjustments to dosing and/or timing of a medication regimen (e.g., by changing the timing and/or content of reminders and/or information provided to a patient), and/or permit information relevant to a patient's condition and/or physiological state to be communicated to the patient and/or another interested party (e.g., such as an advertisement for a product that may treat symptoms that the patient is experiencing, a recommendation and/or contact information or interface to contact a medical provider about the patient's physiological state, or graphical diagnostic information visible to the patient and a healthcare provider to facilitate discussion of the condition). Non-limiting, non-exclusive, examples of other sensors and/or medical devices that may be utilized in communication with or otherwise in conjunction with the device include: glucose monitors (e.g., which may detect a drop in blood sugar for a patient and shorten an interval before the patient's next reminder to take an insulin shot), accelerometers, gyroscopes, vibration sensors, thermometers or other temperature sensors, potentiometers, ohmmeters, voltmeters, light sensors, force sensors, infrared proximity sensors, pressure sensors, pulse sensors, humidity sensors, tilt sensors, magnetometers, blood pressure monitors, smart inhaler devices, pedometers, pulse monitors, prosthetics, implanted devices, pacemakers, cerebral spinal fluid (CSF) flow shunts, muscle relaxant pumps, etc.

In embodiments, the communication module 450 can communicate with other modules and/or other devices to update the medication information 410. For example, the communication module 450 may receive a new drug regimen to update information about medications included in the medication information 410. The communication module 450 may allow medication information 410 for a given patient be updated via any wireless standard or physical connection to the device at a pharmacy, healthcare provider, or user computer. In some embodiments, updates may be received by reading a medium imbedded with a wireless standard. As an illustrative example, a mail-order prescription may include a) medication receptacle 104 (e.g., bottle) with a cap 112 having a detectable tag 114, and b) a card with an RFID chip that can be read by the medication alert device 102 in order to update the device programming to function with the new medication receptacle 104 (e.g., new bottle). The medication alert device 102 may have a designated "synching" interface to initiate an update, such as a button physically integrated into the device or appearing in a display of the medication device 102. The communication module 450 may interface with an optical reader configured to read print on a label on a medication receptacle in order to update medication information 410.

In some aspects, the response module 426 may compare newly received programming instructions to determine if they are more current that currently maintained instructions. The response module 426 may prevent newly received programming instructions from overwriting existing programming instructions if the newly received instructions are older or outdated, relative to the existing programming instructions. In some embodiments, the response module 426 can respond to updated medication information 410 communicated via the communication module 450 by checking if the newly updated medication information 410 corresponds to a patient associated with the medication alert device. If information in the update is not designated for the associated patient, the response module 426 may prevent the update from occurring.

Figure 5:
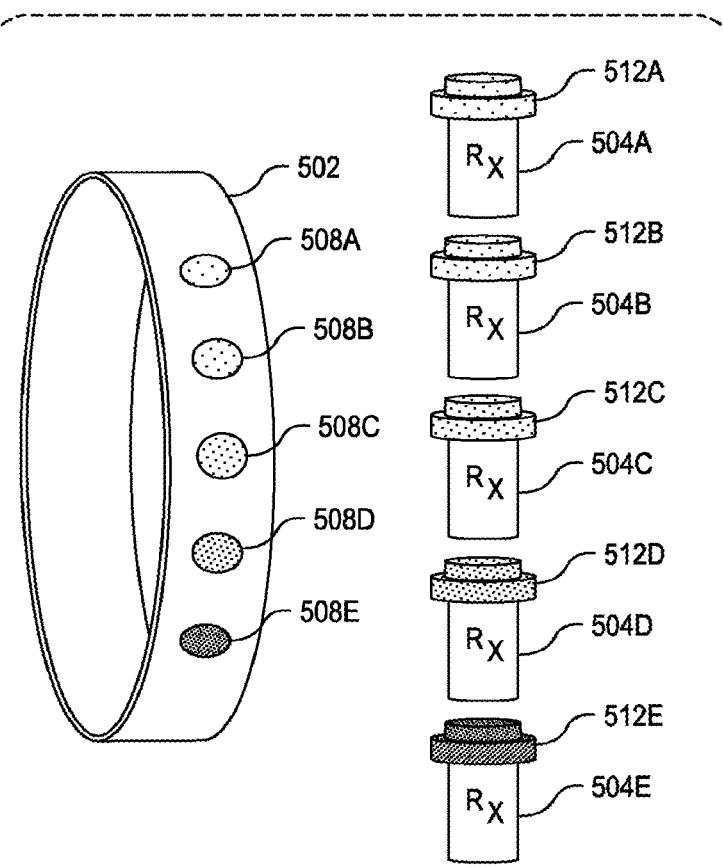
FIG. 5 is a schematic diagram showing an example of a medication alert device and corresponding features of multiple medication receptacles in accordance with at least one embodiment.

FIG. 5 is a schematic diagram showing an example of a medication alert device 502 and corresponding features of multiple medication receptacles 504 in accordance with at least one embodiment. The medication alert device 502 can include a plurality of different color lights 508A-508E, which may each correspond to a different colored cap 512A-512E of different medication receptacles 504A-504E. The lights 508 can provide a simple indicia to indicate which medication corresponds to a particular light. For example, the blue light 508B may flash when it is time for a user wearing the medication alert device 502 to take a medication contained in the medication receptacle 504B having the blue lid 512B. The blue light 508B may persistently flash to provide a reminder to take the medication until the blue lid 512B is removed from the medication receptacle 504B and brought into proximity of the medication alert device 502. The medication alert device 502 may additionally vibrate or emit a sound to draw extra attention to the flashing blue light 508B. When the blue lid 512B is brought into proximity with the medication alert device 502, the medication alert device 502 may detect the proximity and deactivate the flashing blue light 508B.

As described above, in some embodiments, the device 302 and/or the user computer 304 illustrated in FIG. 3 may include a mobile computing device (e.g., a smartphone). Such a mobile computing device may include one more computing systems (e.g., the computer 200 illustrated in FIG. 2).

FIG. 6 and FIGS. 8-17 illustrate the device 302 as a mobile computing device (e.g., smartphone). Such a mobile computing device may include one or more processors (e.g., the processor 260 illustrated in FIG. 2) configured to execute a set of instructions stored within a non-transitory, computer-readable medium (e.g., stored within the file storage subsystem 268 of the device 302, as illustrated in FIG. 2, or a remote file storage subsystem of a server). The set of instructions may correspond to a software application 602 (e.g., a medication management application). The following figures are used to show and describe potential features of the software application 602. It is understood that the features of the software application 602 may be equally performed by other forms of the device 302. For example, the device 302 may additionally or alternatively include a tablet computing device, a wearable computing device (e.g., FITBIT, APPLE WATCH, etc.), a laptop computing device, a desktop computing device, a computing device associated with a smart speaker (e.g., a smart speaker with a virtual assistant, such as SIRI, ALEXA, GOOGLE ASSISTANT, BIXBY, or CORTANA), a pager, a computing device embedded within a smart household appliance (e.g., television, refrigerator, stove, oven, microwave oven, toaster, dishwasher, washing machine, dryer, blender, vacuum cleaner, etc.), or a computing device embedded within a medication container (e.g., a pill bottle).

In order to carry out various functions of the software application 602, the device 302 may communicate with one or more servers (e.g., communicate with cloud servers via a network 306, such as the public Internet). Such servers may correspond to the third party computer 308, in some embodiments. While various functions and features may be shown and described herein as being carried out by the device 302, it is understood that any individual feature may equally be executed on the one or more servers. For example, as herein shown and described, the device 302 may execute image analysis on a captured image to determine information about the captured image (e.g., determine a number of pills present in the image). It is understood that, instead, the captured image could be transmitted to the one or more servers, and the one or more servers could perform the same image analysis (e.g., and then send the result to the device 302). Similarly, while some data (e.g., medical information about a patient) may be described as being stored on one or more servers, it is understood that such data could additionally or alternatively be stored locally on the device 302.

In some embodiments, the instructions of the software application 602 may be executed by one or more processors of the device 302 (e.g., a mobile computing device) to enable the device 302 to perform one or more medication management functions. For example, the software application 602 may be executed to enable the device 302 to capture information about a medication label associated with a medication. Further, the software application 602 may be executed to enable the device 302 to analyze the information about the medication label to extract medication information. In addition, the software application 602 may be executed to enable the device 302 to generate a medication schedule for a corresponding patient associated with the medication. The medication schedule may include a dosage strength and dosage frequency. Still further, the software application 602 may be executed to enable the device 302 to prompt the corresponding patient to take an amount of the medication corresponding to the dosage strength at a predetermined time according to the medication schedule. Yet further, the software application 602 may be executed to enable the device 302 to receive an indication that the corresponding patient has taken the amount of the medication corresponding to the dosage strength.

Additionally or alternatively, in some embodiments, a remote computing device (e.g., a server, such as the third party computer 308 illustrated in FIG. 3) may have instructions stored thereon (e.g., stored on a non-transitory, computer-readable medium such as a file storage subsystem 268, as illustrated in FIG. 2) that, when executed by a processor, perform a method. The method may include receiving information, from a computing device (e.g., the device 302), about a medication label associated with a medication. The method may also include analyzing the information about the medication label to extract medication information. Further, the method may include generating a medication schedule for a corresponding patient associated with the medication. The medication schedule may include a dosage strength and dosage frequency. In addition, the method may include transmitting, to the computing device, the medication schedule for the corresponding patient. Still further, the method may include receiving, from the computing device, an indication that the corresponding patient has taken an amount of the medication corresponding to the dosage strength. The indication that the corresponding patient has taken the amount of the medication corresponding to the dosage strength was received by the computing device in response to the computing device prompting the corresponding patient to take the amount of the medication corresponding to the dosage strength at a predetermined time according to the medication schedule.

Figure 6:
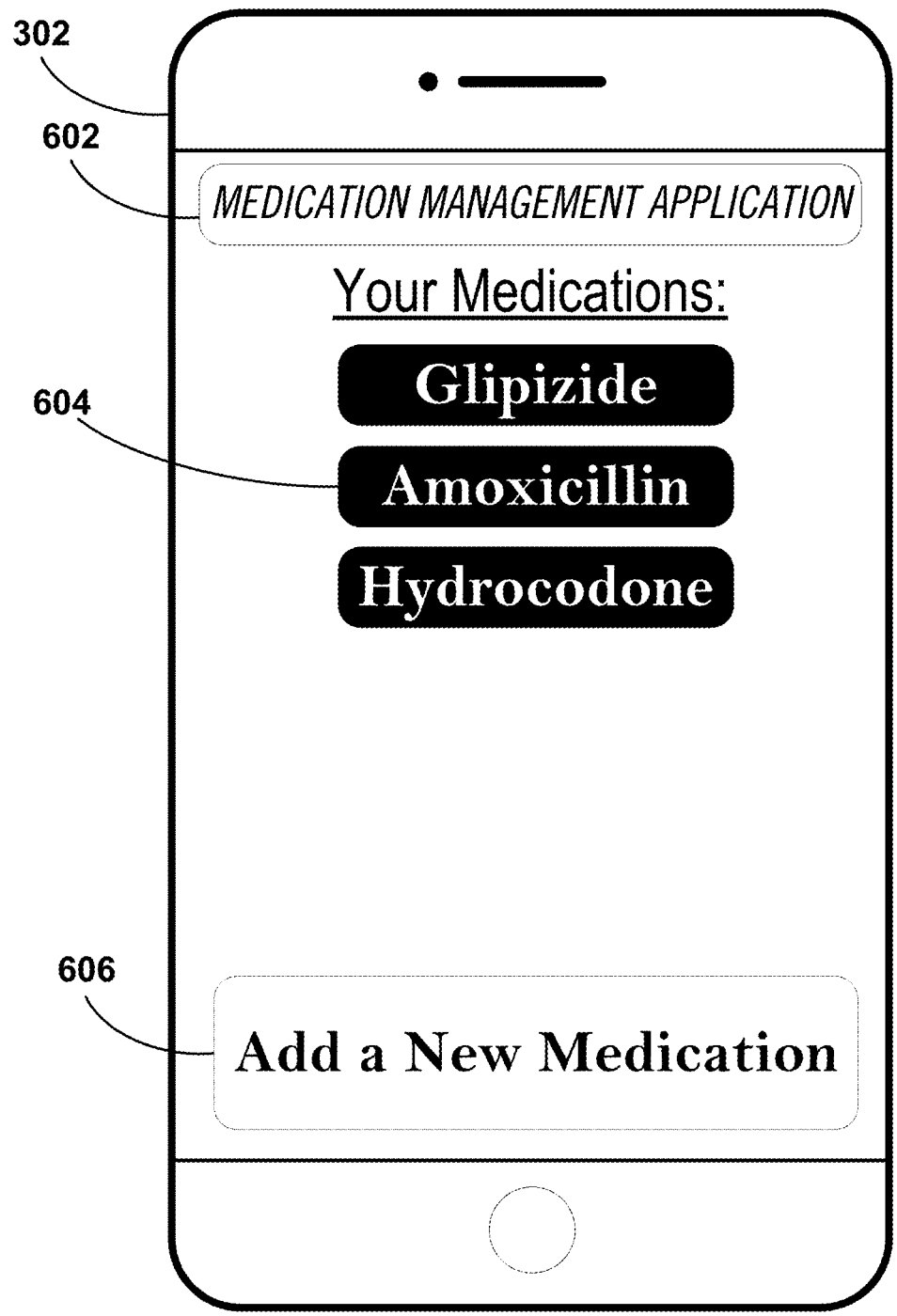
FIG. 6 is an illustration of a medication management application executed by a mobile computing device in accordance with at least one embodiment.

FIG. 6 illustrates features of the software application 602, according to example embodiments. The software application 602 may be a medication management application, for example. The screen illustrated in FIG. 6 may correspond to a "home screen," in some embodiments. In order to access the software application 602, a user may have to enter a set of authentication credentials (e.g., username and password) that are authenticated against proper credentials (e.g., stored within a server that hosts the software application 602). As illustrated, any previously added medications 604 that the patient takes may be listed. The previously added medications 604 may each be individually selected by the user to view more information about the respective medication 604, for example. Further, a button 606 may be displayed that enables a user to add an additional medication for a patient.

Figure 8:
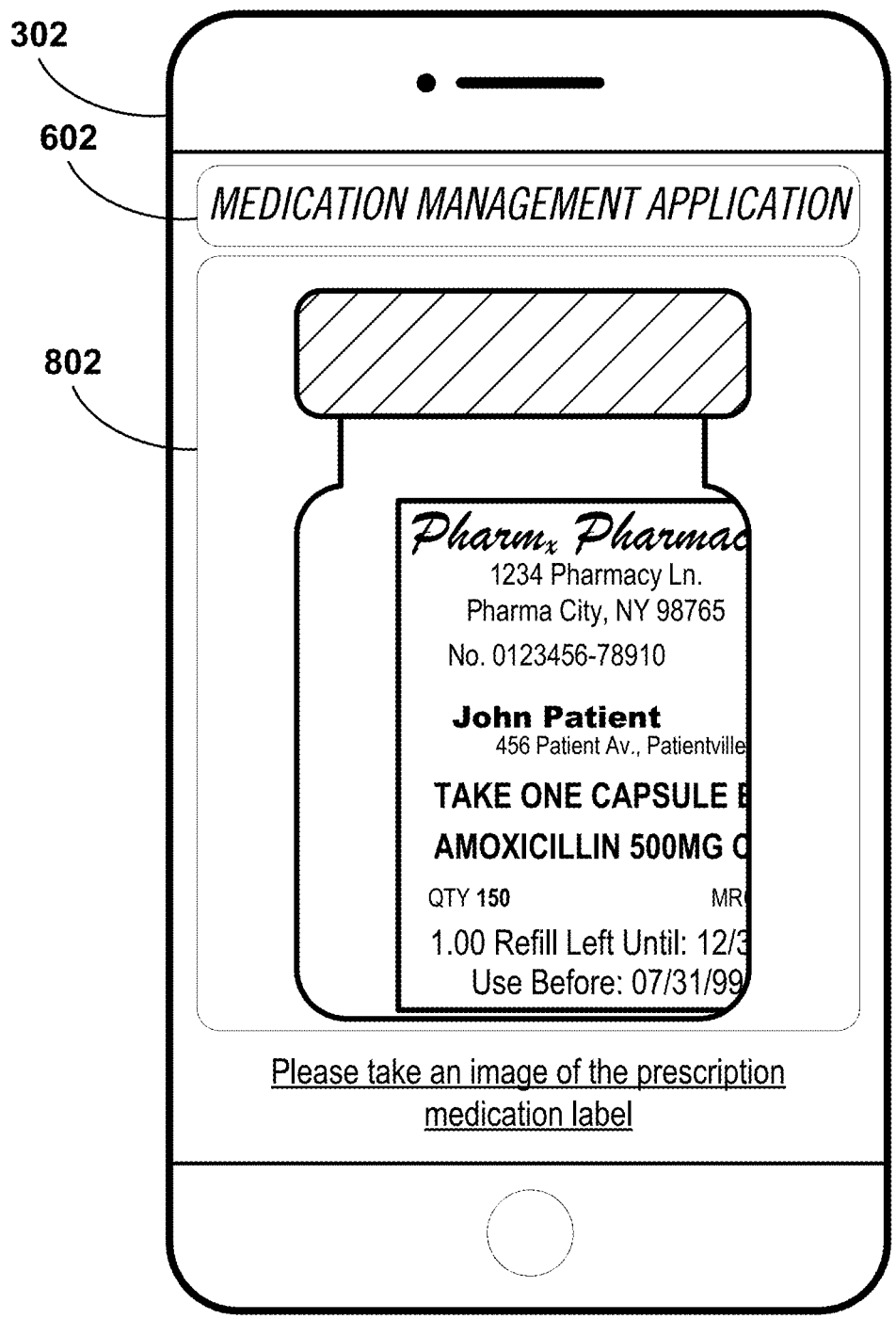
FIG. 8 is an illustration of a medication management application executed by a mobile computing device in accordance with at least one embodiment.
Figure 9:
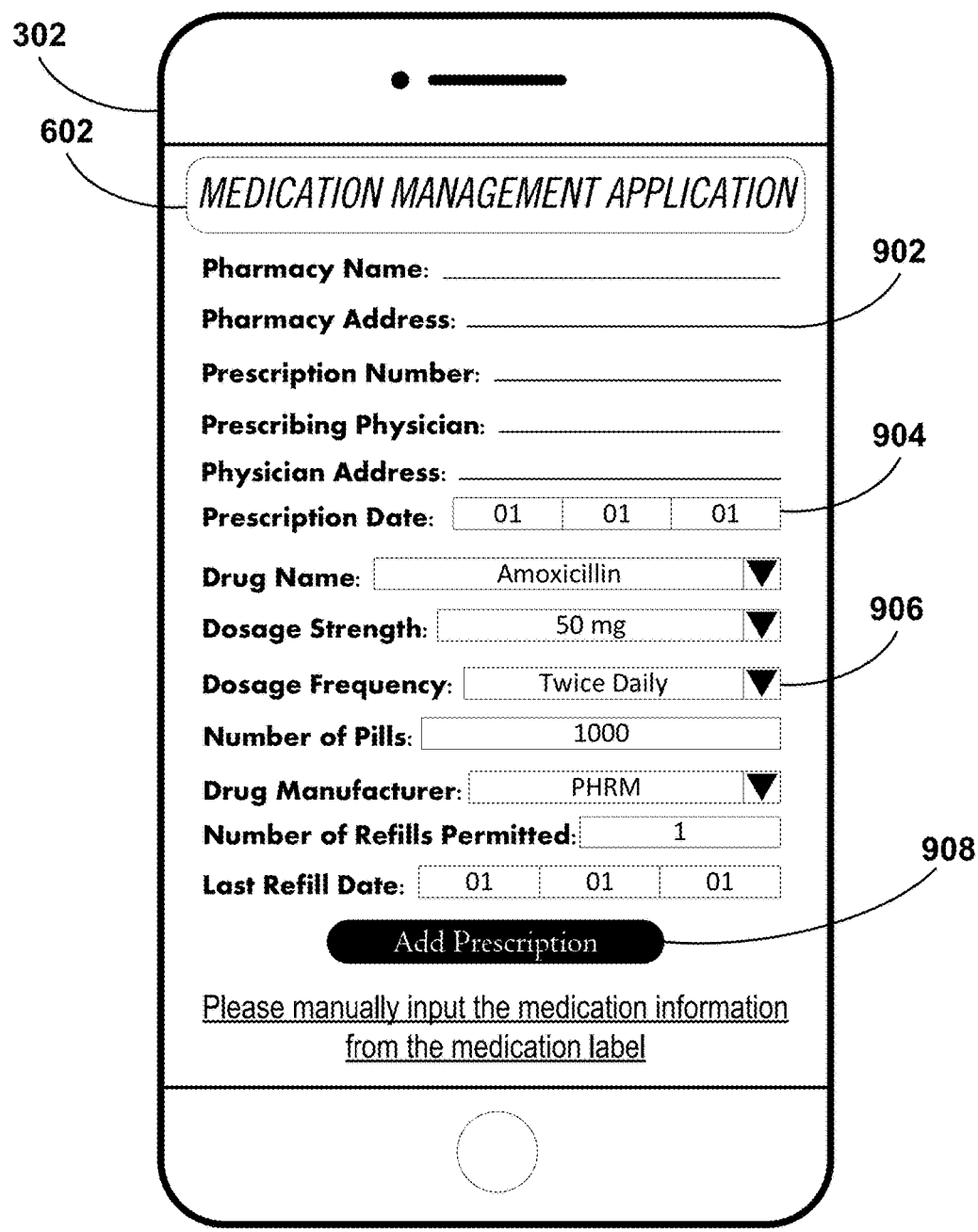
FIG. 9 is an illustration of a medication management application executed by a mobile computing device in accordance with at least one embodiment.

When selected, the button 606 may change the display of the software application 602 to the displays illustrated in FIG. 8 or FIG. 9, for example.

Figure 7:
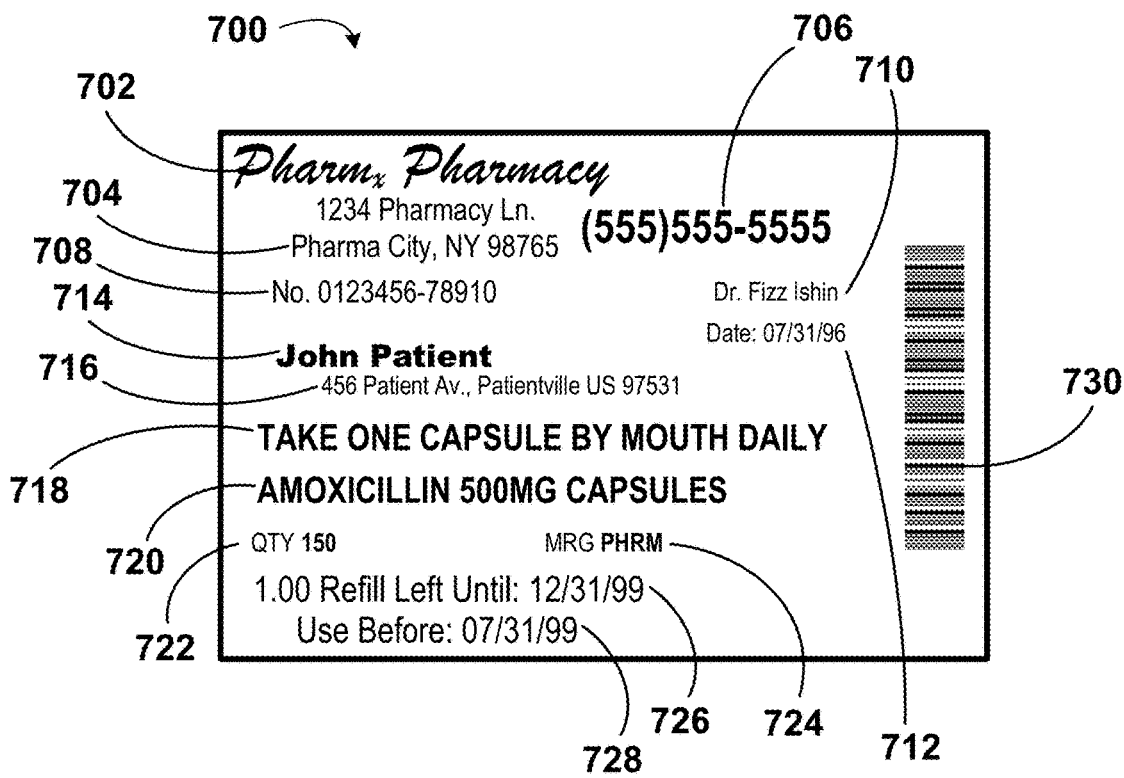
FIG. 7 is an illustration of a medication label in according with at least one embodiment.

FIG. 7 illustrates a medication label 700. The medication label 700 may be for a prescription medication or an over-the-counter medication, in various embodiments. Medication labels 700 may correspond to various types of medication (e.g., pills, creams, ointments, syrups, serums, comestibles, or injectionables, etc.). As illustrated, the medication label 700 may include a variety of information. For example, the medication label 700 may indicate a pharmacy 702, a pharmacy address 704, a pharmacy phone number 706, a prescription serial number 708, a prescribing physician 710, a prescription date 712, a patient name 714, a patient address 716, prescription instructions 718, a drug type 720, a drug quantity 722, a pharmaceutical manufacturer 724, prescription refill information 726, expiration date 728, and a prescription barcode 730. The information present on the medication label 700 may be extracted (e.g., via an image processing algorithm on an image of the medication label 700 captured by a camera of the device 302) to generate a medication schedule for a patient, for example.

In some embodiments, the pharmacy 702 may be indicated on the medication label 700 using the name of the pharmacy. Additionally or alternatively, the pharmacy 702 may be indicated on the medication label by a logo of the pharmacy (e.g., including a specific color and/or design).

The prescription instructions 718 may include a drug dosage strength (e.g., in milligrams or number of pills) and/or a dosage frequency (e.g., in number of times per day).

The prescription barcode 730 may include all of the other information on the medication label 700 in a concise, computer-readable form. In some embodiments, the prescription barcode 730 may be replaced by or supplemented by one or more other codes (e.g., a QUICK-RESPONSE (QR) code).

In other embodiments, the medication label 700 may include less information, additional information, or alternative information. For example, the medication label 700 may include a phone number of the prescribing physician, a website of the pharmacy, a website of the prescribing physician, an email address of the prescribing physician, an email address of the pharmacy, a name of the pharmacist who filled the prescription, an email address of the pharmacist who filled the prescription, a price for the prescription, information about the insurance policy used to pay for the prescription, initials of the patient (e.g., first initial of first name and first initial of last name), a patient identification (ID) number, a patient's date of birth, a proprietary name of the prescribed drug, and/or a generic name of the prescribed drug.

FIG. 8 illustrates features of the software application 602, according to example embodiments. As illustrated, the software application 602 may allow for the capture of an image. Such an image may be captured in an omnibus scanning region 802. The omnibus scanning region 802 may provide a view of a scene as captured by a camera (e.g., a smartphone camera or other camera connected to the device 302). Further, the omnibus scanning region 802 may be used by the software application 602 to capture images of a variety of objects (e.g., medication labels, medication bottles pills themselves, diagnostic testing devices, such as a scale or blood glucose sensor). As illustrated in FIG. 8, the omnibus scanning region 802 may be used to capture an image of a medication label on a prescription medication bottle. Once the image of the medication label is captured, the image may be stored within a storage of the device 302 (e.g., a file storage subsystem 268, such as a hard drive). Additionally or alternatively, the image may be transmitted to a server (e.g., a third party computer 308) associated with the software application 602 and stored within a storage of the server (e.g., cloud storage).

Once the image is stored within a storage of the device 302 and/or a server, image analysis may be performed on the image to extract information about the medication from the medication label in the image. Such image analysis may be performed on either or both of the device 302 and the server. The image analysis/information extraction may include a variety of image processing techniques. In some embodiments, prior to extracting information from the image, the image may be manipulated into a standardized/computer-readable form. For example, the image may be flattened, filtered (e.g., by subtracting background noise), cropped, scaled, etc. Further, in order to extract the information from the image, the image analysis/information extraction may include machine learning (e.g., using an object classifier that was previously trained using labeled training data from a database associated with the software application 602). Additionally or alternatively, optical character recognition (OCR) may be performed on the image and then the relevant information from the medication label could be read from the label (e.g., by a processor of the device 302 executing instructions of the software application 602). In some embodiments (e.g., embodiments where the medication label in the captured image contains a barcode or other code, such as the prescription barcode 730), the image analysis/information extraction may only include scanning the image for a code (e.g., barcode or QR code), identifying a code, reading the code, and then extracting all the medication information from the medication label using only the code.

Regardless of the method by which the information is retrieved from the image, the information may be stored as medication information for a given medication of a given patient (e.g., based on the patient name 714 and patient address 716 fields of the medication label). This information may later be used by the software application 602 (e.g., executed on the device 302 and/or executed on a server) to perform an action (e.g., generate a medication schedule for the patient or alert a physician or pharmacist that a prescription has been filled by the patient). Additionally or alternatively, in some embodiments, this information extracted from the image can be compared to information about a patient stored in a database (e.g., within the device 302 or a server associated with the software application 602) to ensure accuracy. For example, a date of birth of the patient, a name of the patient, an address of the patient, etc. can be compared with previously stored information associated with the patient who is using the device 302 and/or the patient who is known to be associated with the medication label in the captured image.

In alternate embodiments, in addition to or instead of capturing an image of the medication label 700, an image of the physical medication may be captured in the omnibus scanning region 802 of the software application 602. For example, an image of pills, creams, injectionables, etc. may be captured in the omnibus scanning region 802. Using image processing techniques, such an image of the physical medication may be used to provide some information about the relevant prescription. For example, a captured image of a given type of pill (e.g. amoxicillin) may be analyzed by an image analysis portion of the software application 602. The image analysis may compare certain features of the pill (e.g., color, size, shape, symbols on the pill, etc.) to features of various labelled images of pills in a repository stored on a server (e.g., a repository from a governmental agency, such as the national institute of health a repository from a pharmaceutical company, or a repository associated with the software application 602 itself). This may allow the software application 602 to determine what type of pill is in the captured image, a dosage strength of the pill, a typical dosage frequency associated with the captured pill, etc.

In still other embodiments, in addition to or instead of capturing an image of the medication label 700, an image of medical paperwork from a healthcare provider (e.g., hospital discharge paperwork from a physician to a patient, pharmaceutical instructions from a pharmacist to patient, paperwork from an insurance provider, etc.) may be captured by the omnibus scanning region 802 of the software application 602. Similarly to above, a captured image of such paperwork could undergo image analysis to extract medication information corresponding to a patient. Further, in some embodiments, the medical paperwork may include additional information that is stored within a repository corresponding to the software application 602 (e.g., a server or a storage of the device 302). Such additional information may include times at which certain health maintenance activities are to be performed by the patient (e.g., performing a certain type of exercise for a certain length of time, performing an at-home diagnostic test, scheduling a follow-up appointment with a physician, etc.).

In some embodiments, performing image processing on a captured image may include determining if the captured image is blurred, obscured, or otherwise partially or wholly unusable. If it is determined that the captured image is partially or wholly unusable for some reason, the software application 602 may prompt a user of the device 302 to capture an additional image. The additional image may be more clear, and therefore, may allow the medication information to be extracted using image processing. After the additional image is captured, image processing may be performed on the additional image. If the additional image is also determined be partially or wholly unusable for some reason, the software application 602 may prompt a user to enter the medication information from the medication label 700 manually (e.g., as illustrated in FIG. 9).

In some embodiments, in addition to or instead of capturing an image using the device 302 (e.g., in the omnibus scanning region 802), audio or video footage may be captured and analyzed. For example, video or audio of a pharmacist or physician providing medication instructions may be recorded. Then, such a recording could be analyzed to extract medication information (e.g., in order to produce a medication schedule based on dosage strength and dosage frequency described by the physician or pharmacist).

FIG. 9 illustrates features of the software application 602, according to example embodiments. FIG. 9 illustrates a feature by which a user (e.g., a patient, a physician, a healthcare provider, a pharmacist, a benefits manager, an insurance company official, a nurse, a hospital employee, a grocery store employee, a care coordinator, a claims processor, or another approved party) can enter patient medication information into the software application 602 manually. The medication information can be entered using various types of fields, such as text fields 902, calendar fields 904, and drop-down menus 906. The fields may include a pharmacy name field, a pharmacy address field, a prescription number field, a prescribing physician field, a prescribing physician address field, a prescription date field (e.g., when the prescription was written or when the prescription was filled), a drug name field, a dosage strength field, a dosage frequency field, a number of pills field, a drug manufacturer field, a number of refills permitted field, and a last refill date field. It is understood that other types of information fields are also possible. Additionally, once all the medication information for a given medication has been entered, a button 908 may be engaged to commit the medication information to a repository (e.g., to a storage of the device 302 and/or of a server associated with the software application 602).

As illustrated, patient name/patient address are not listed as fields that can be entered. This is because the instance of the software application 602 may already be linked to a specific patient, and thus, the software application 602 may already be aware of the patient to which the medication information corresponds. However, in some embodiments (e.g., in embodiments where pharmacists or physicians are using the software application 602 to enter information for multiple patients at various times), there may be fields for patient name, patient address, patient social security number, patient ID number, etc.

In some embodiments, some of the fields may auto-populate based on medication information stored within a storage corresponding to the software application 602 (e.g., stored within a database on a server). For example, if a given patient refills a specific prescription at a specific frequency (e.g., contraceptive prescription refilled monthly), each time the medication is refilled (e.g., each month), the medication information for that specific prescription may auto-populate and then the user of the software application 602 can update/modify the information, as necessary. As another example, when a user selects a drug name and drug manufacturer, some of the remaining fields may auto-populate with information based on information about the selected drug from a pharmaceutical company's repository or website.

In some embodiments, there may be fields or additional sections of the software application 602 for additional information, such as health maintenance information or insurance information. For example, there may be an additional section of the software application 602 where insurance information (e.g., information from an insurance card) or identification information (e.g., information from a driver's license) can be entered for a patient, stored for a patient, and, later, displayed for a patient. Additionally or alternatively, calendar information (e.g., scheduled work-outs or future appointments with one or more physicians) may be entered manually. Further, in some embodiments, a physician may manually enter other instructions for a patient (e.g., exercise recommendations regarding type and frequency of exercise, referrals for other physicians, etc.). In some embodiments, one or more users of the software application 602 may enter one or more informational reminders (e.g., contact information and/or location information for hospitals, insurance companies, pharmacists, care coordinators, etc.).

In various embodiments, regardless of the technique by which the medication information is input into the software application 602 (e.g., using the omnibus scanning region 802 as in FIG. 8 or entered manually as in FIG. 9), the medication information may be used to generate a medication schedule for a corresponding patient. The medication schedule may be generated by a computing device (e.g., by the device 302 or by a server, such as the third party computer 308). Further, the medication schedule may include a dosage strength of a medication and/or a dosage frequency of a medication (e.g., take 50 mg of a certain drug between the hours of 8:00 AM and 9:00 AM every day). Such dosage strength and frequency may be based on the dosage strength and frequency from the medication label, for example. The dosage frequency may be used to set times (e.g., morning, noon, night, etc. or 9:00 AM, 12:00 PM, 6:30 PM, etc.) throughout the day when a given medication is to be taken. Additionally, other stored health information about the patient may be taken into account (e.g., stored information about the patient's height, weight, gender, age, stage of medication condition, length of time the patient has been taking the medication, or doctor's recommendations) in order to generate or modify the medication schedule. For example, the medication schedule may be updated in response to a patient losing or gaining weight, a condition of the patient worsening or improving, or a patient aging. Such information could be self-reported by a patient (e.g., by conducting an at-home diagnostic test, such as weighing themselves and reporting the weight using the software application 602) or could be reported to the software application 602 by a medical professional (e.g., a physician or a nurse after performing a diagnostic test). After being generated, the medication schedule may be used to provide reminders to a patient to take their medication (e.g., as shown and described with references to additional figures below).

In some embodiments, medication information may be captured from medication labels of two or more different medications. In such embodiments, the two or more different medications may each be included in generated medication schedules (e.g., with separate dosage strengths and/or dosage frequencies). In addition, the computing device (e.g., the device 302 or a server) generating the medication schedules for each of the medications may take any adverse drug interactions that exist among the medications into account. For example, if a first medication includes daily calcium supplements and a second medication includes tetracycline antibiotics (e.g., for treatment of acute urinary tract infections), the times at which the daily calcium supplements are to be taken may be staggered from the times at which the tetracycline antibiotics are to be taken (e.g., staggered by 2 or more hours), because calcium supplements and tetracycline antibiotics are known to have potential adverse drug interactions with one another if taken in close temporal proximity. Such staggering based on potential adverse drug interactions among two or more medications may prevent negative health consequences for a patient while maintaining proper dosage strengths and dosage frequencies for each of the medications. Further, as additional medications are added or removed from a repository (e.g., removed from a data storage corresponding to the software application 602, such as a server, by a user of the device 302), the medication schedule for each of the remaining medications may be updated. Using the example above, if the tetracycline antibiotics no longer need to be taken by a corresponding patient, the medication schedule for the tetracycline antibiotics may be deleted and the calcium supplement medication schedule may be adjusted to reflect the fact that there are no longer any potential adverse drug interactions among the medications being taken by the patient.

The medication schedule(s) may be stored locally (e.g., on a file storage subsystem 268 of the device 302) and/or remotely (e.g., on a file storage subsystem 268 of a server, such as the third party computer 308). In addition, in some embodiments, one or more physicians of a corresponding patient may have access to the generated medication schedule(s). Further, a record associated with the corresponding patient may be kept in the software application 602 (e.g., stored locally within the device 302 and/or stored remotely within a server) regarding the past times at which the corresponding patient took specific medications (i.e., a medication compliance log may be maintained). This medication compliance log may be used by physician(s) to discuss compliance with the corresponding patient or to modify a treatment regimen for the corresponding patient.

Still further, the medication schedule may be supplemented and/or replaced by a treatment schedule in some embodiments. A treatment schedule may include workouts for a corresponding patient at specified times, at-home diagnostic tests for a corresponding patient at specified times (e.g., blood glucose testing for a diabetic patient), trips to one or more physicians' offices for the corresponding patient, specified meal plans (e.g., in terms of foods and/or specified mealtimes) for the corresponding patient, and a specified sleeping schedule for the corresponding patient.

Figure 10:
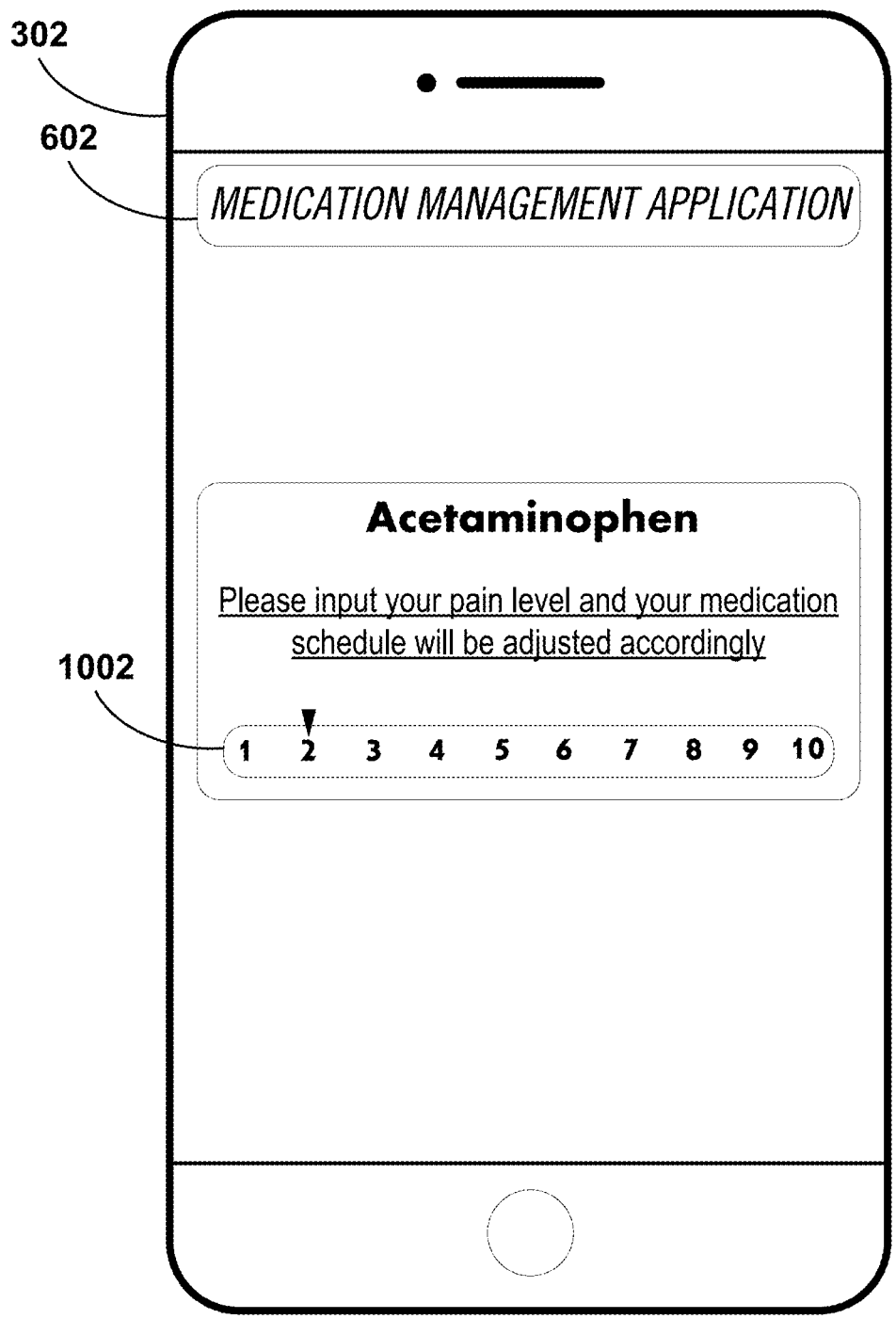
FIG. 10 is an illustration of a medication management application executed by a mobile computing device in accordance with at least one embodiment.

FIG. 10 illustrates features of the software application 602, according to example embodiments. As illustrated, the software application 602 may capture context 1002 relating to the present state of the patient corresponding to the software application 602. The context 1002 can be used to modify a medication schedule (e.g., the medication schedule previously generated based on the medication information from the medication label). The example illustrated in FIG. 10 includes the software application 602 receiving input from a patient regarding a pain level of the patient. Based on the indicated pain level, the medication schedule may be adjusted accordingly (e.g., a dosage strength and/or dosage frequency of an associated medication may be modified according to the pain level). For example, if a patient has a high level of pain, the dosage strength for the next scheduled dose of acetaminophen may be increased.

In other embodiments, other context information may be received and/or used to modify medication schedules. For example, context can include time (e.g., 10:00 AM), time of day (e.g., morning), location of user (e.g., global positioning system (GPS) coordinates based on the location of the device 302), properties of the patient's environment (e.g., weather, temperature, ultraviolet (UV) levels, smog levels, air quality metrics, etc.), the patient's medication history (e.g., which medications they are scheduled to take and the patient's adherence to medication schedules), the patient's health history (e.g., medical conditions of the patient, medical conditions for which the patient has received treatment, locations where the patient has previously been treated, where the patient receives their medication, costs of medication in surrounding locations when the patient filled a given medication prescription, locations of healthcare providers of the patient, distance between patient's home and healthcare providers and/or pharmacies, distance between patient's place of employment and healthcare providers and/or pharmacies, etc.).

Figure 11:
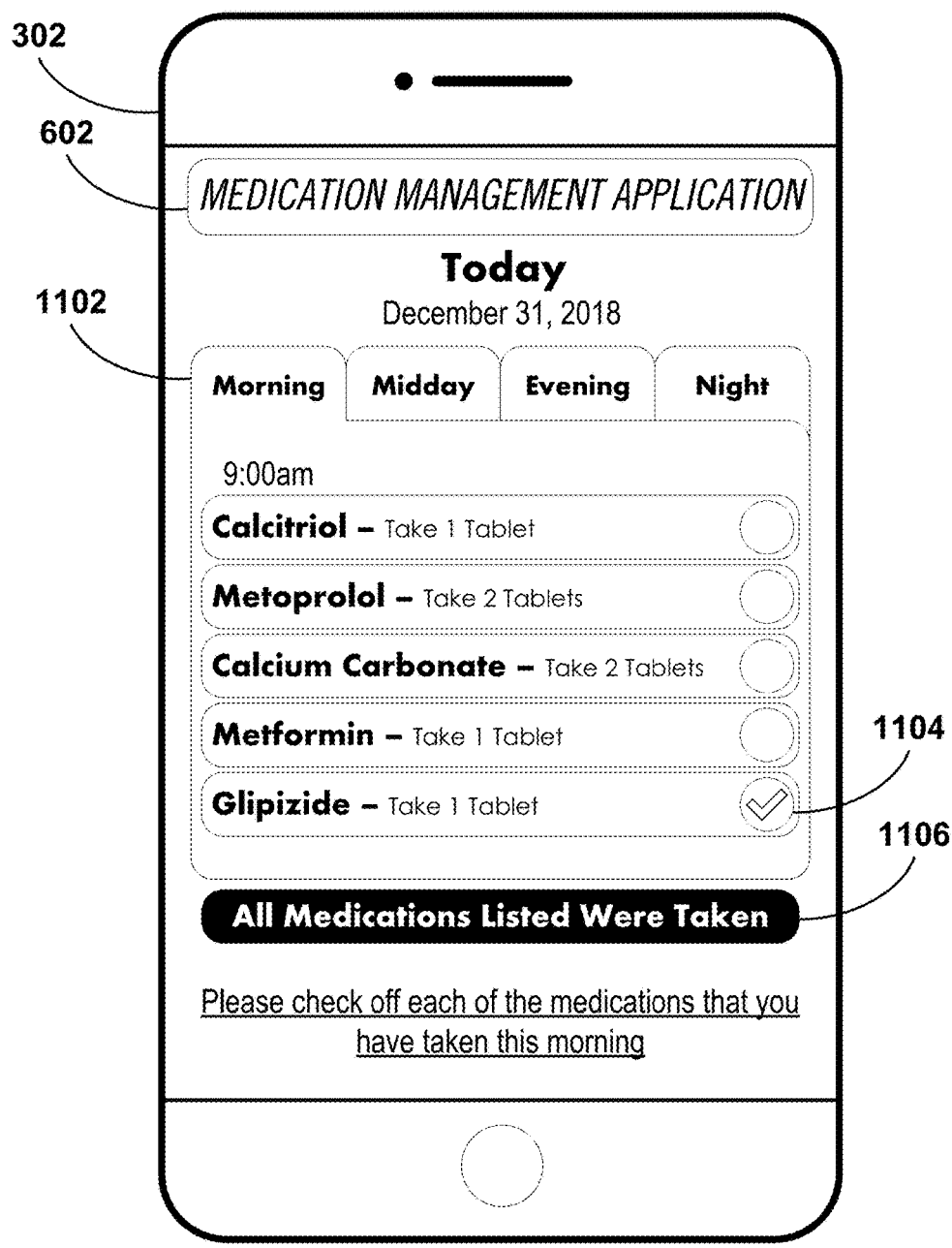
FIG. 11 is an illustration of a medication management application executed by a mobile computing device in accordance with at least one embodiment.

FIG. 11 illustrates features of the software application 602, according to example embodiments. The feature illustrated in FIG. 11 may allow a user to enter into the software application 602 which medications have been taken on a given day based on one or more generated medication schedules. As illustrated, the feature may include one or more time of day tabs 1102, one or more check boxes 1104, and a select all button 1106. The time of day tabs 1102 may allow a user (e.g., a patient or healthcare provider) to select different times of day at which one or more medications may be scheduled to be taken based on their generated medication schedules. The check boxes 1104 may allow a user (e.g., a patient or healthcare provider) to select those medications that were taken at the indicated time. For example, in FIG. 11, the corresponding patient may have taken one tablet of glipizide at 9:00 AM. Because in at least some cases a patient will have taken all medication scheduled for an indicated time, the select all button 1106 may conveniently place a check in the check boxes 1104 next to each medication listed at the indicated time.

A list (e.g., stored within the device 302 and/or on a server) may be updated based on the medications that are indicated as taken to reflect which of the medications were taken by the corresponding patient (i.e., an medication adherence log may be updated). As described above, in some embodiments such a list can be viewed by a healthcare provider (e.g., physician or nurse). Such a healthcare provider may view the list on the device 302 or on another device (e.g., third party computer 308) executing a different instance of the software application 602, in various embodiments.

In some embodiments, in addition to or instead of selecting medications that have been taken manually, a user of the device 302 may input the medications as an image (e.g., via a camera using the omnibus scanning region 802). The image may be a captured image of the medication immediately prior to a patient taking the medication (e.g., a picture of a pill immediately prior to the patient ingesting the pill), for example. Using an image processing algorithm (e.g., object recognition or OCR), a processor (e.g., of the device 302 or of a server) may extract type of medication and/or quantity of medication taken by the patient from the captured image. Using the information extracted by the image processing algorithm, the computing device (e.g., the device 302 or a server) may update a list of medications taken by a corresponding patient.

In still other embodiments, such as embodiments where the device 302 includes a smart speaker (e.g., a smart speaker with a virtual assistant, such as SIRI, ALEXA, GOOGLE ASSISTANT, BIXBY, or CORTANA), rather than selecting medications that have been taken manually, a user of the device 302 may provide spoken confirmation as to which medications have been taken by the corresponding patient. For example, a user of the device 302 may say, "I have taken 250 mg of ibuprofen at 3:07 PM." Such spoken confirmation may be captured by the software application 602.

Figure 12:
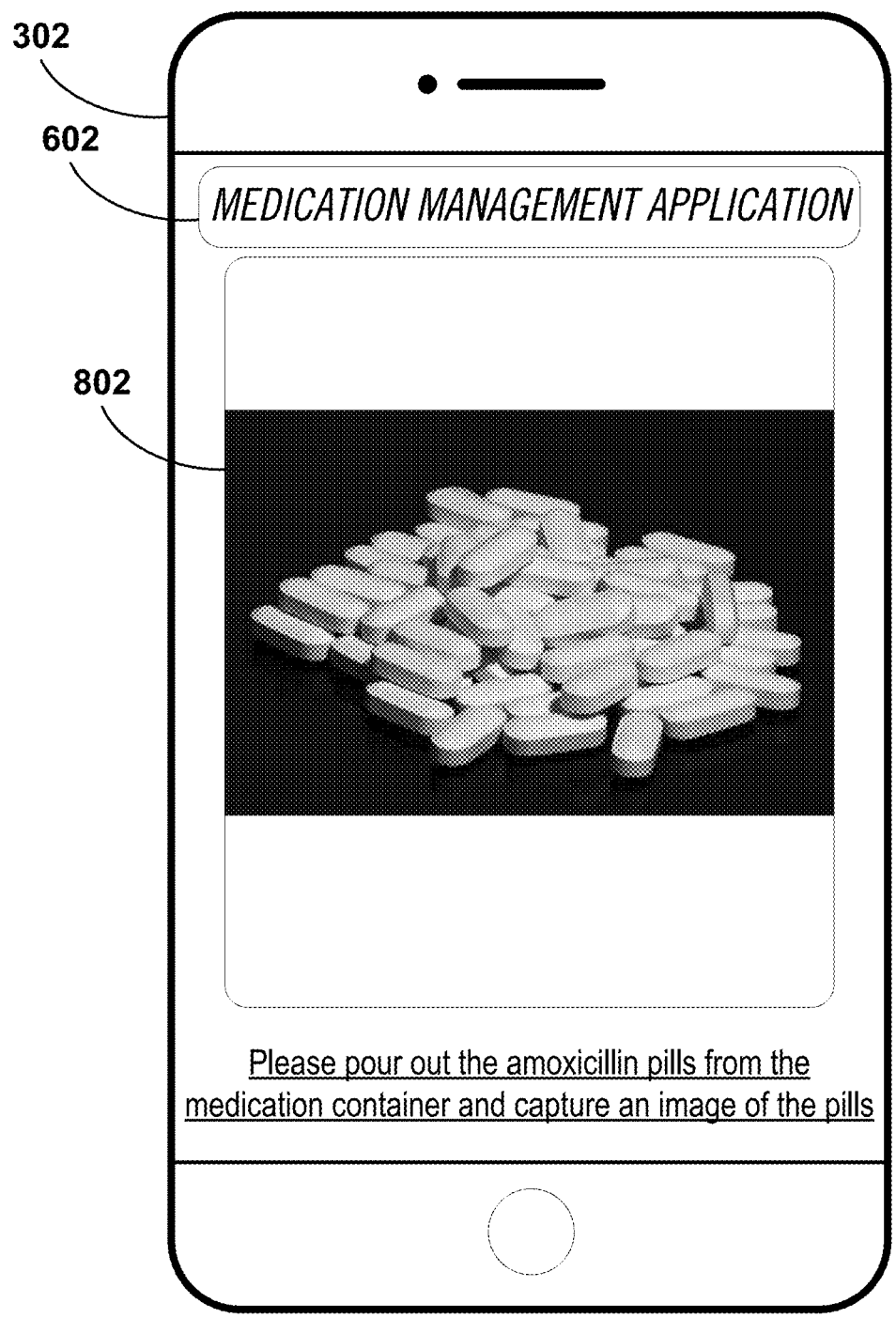
FIG. 12 is an illustration of a medication management application executed by a mobile computing device in accordance with at least one embodiment.

FIG. 12 illustrates features of the software application 602, according to example embodiments. The features of FIG. 12 may represent a technique by which the software application 602 determines an amount of remaining medication within a given prescription and/or medication container (e.g., a number of pills remaining in a pill bottle). As illustrated in FIG. 12, medication (e.g., pills) may be poured out (e.g., onto a solid background, such as a countertop with a white or black background) and then captured using a camera (e.g., via the omnibus scanning region 802). Using image analysis (e.g., object recognition, edge detection, shape matching, color matching, text matching, texture matching, OCR, etc.), the amount of medication remaining may be counted (e.g., the number of pills remaining may be counted). Counting the amount of medication remaining may include comparing portions of the captured image to information from a repository (e.g., pill color, pill shape, and/or pill size stored within a government server, such as a publicly available NIH repository).

Alternatively, an image of a scale may be used to determine the amount of medication remaining in a prescription. For example, a user may capture an image of a tube of ointment on the scale. Such an image may be captured using a camera (e.g., via the omnibus scanning region 802). Using image analysis (e.g., OCR), a computing device may determine the weight of the ointment on the scale based on a reading of the scale in the captured image. Then, by subtracting a known weight of the tube (e.g., stored within a repository associated with the software application 602, either in the device 302, in a server associated with the software application 602, and/or a server of a government agency, such as the NIH, or publicly available server of a pharmaceutical company) and dividing by the known weight of a single dose for the corresponding medication (e.g., also stored within a repository associated with the software application 602, either in the device 302, in a server associated with the software application 602, and/or a server of a government agency, such as the NIH, or publicly available server of a pharmaceutical company), the number of doses of medication (e.g., cream) remaining in the prescription may be determined.

In still other embodiments, rather than capturing an image to determine an amount of remaining medication, the amount of medication remaining in a prescription may be tracked from an initial medication quantity (e.g., as extracted from a medication label) based on each time a corresponding patient takes the medication and in what quantity the medication is taken. For example, if a patient receives a prescription with 150 pills in a pill container (e.g., as indicated on the medication label), an initial amount of medication may be set to 150 pills. Then, as the patient begins to take the medication, the number of remaining pills may be decremented. For example, if a patient takes 1 pill in the morning, the patient may indicate on the software application 602 (e.g., manually using the device or by capturing an image of the pill using a camera before ingesting the pill) that 1 pill has been taken. Thus, the number of remaining pills (e.g., an integer of remaining medication stored within the device 302 and/or within a server associated with the software application 602) may be reduced from 150 to 149.

Regardless of how the amount of medication is monitored, the device 302 and/or a server associated with the software application 602 may contact a pharmacy to refill a prescription once the amount of medication remaining falls below a threshold value (e.g., a threshold value previously set by the patient, by a pharmacy, or by a physician or a default threshold value equal to some percentage of the total initial medication, such as 20%, 10%, 5%, 1%, etc.). The pharmacy that is contacted to refill the prescription may be the nearest pharmacy to the patient's home address, in some embodiments. In other embodiments, the pharmacy that is contacted to refill the prescription may be the pharmacy listed on a medication label associated with the medication initially captured (e.g., via a camera) by the device 302 (e.g., as illustrated in FIG. 8). Further, before contacting a pharmacy to refill the prescription, the medication information (e.g., from the medication label of the medication captured by a camera previously) may be consulted (e.g., by the device 302 or a server associated with the software application 602) to confirm that a refill of the prescription is allowed by the prescribing physician/pharmacist (e.g., the prescription refill information 726 may be checked). If one or more refills are permitted, the pharmacy may be contacted to initiate a refill. If refills are not permitted, the pharmacy may not be contacted.

Figure 13:
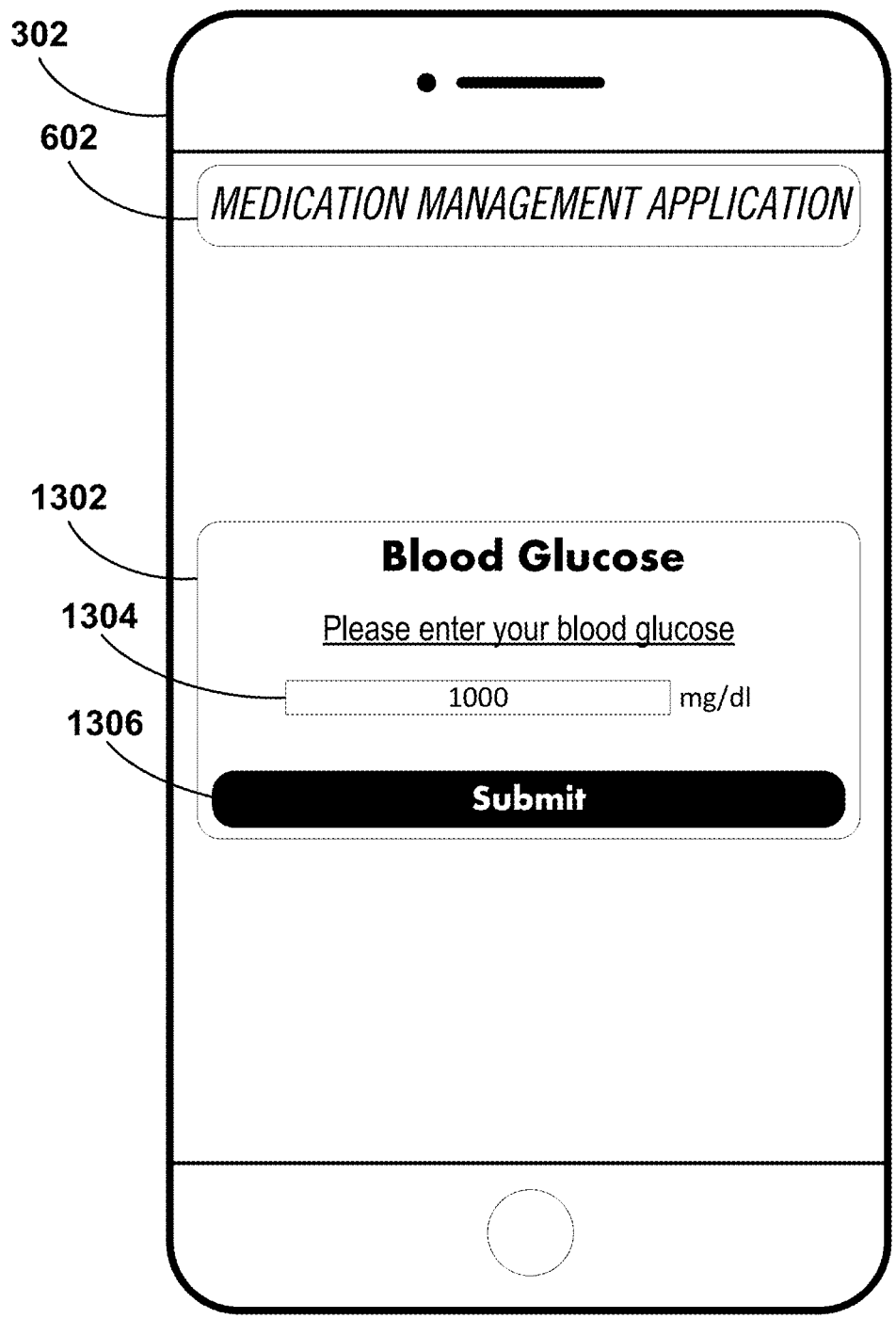
FIG. 13 is an illustration of a medication management application executed by a mobile computing device in accordance with at least one embodiment.

FIG. 13 illustrates features of the software application 602, according to example embodiments. In some embodiments, the software application 602 may prompt a patient to enter health information (e.g., based on an at-home diagnostic test). As illustrated, the device 302 may display to a user of the device 302 (e.g., a patient, a physician, or an approved third party) a health information box 1302. The health information box 1302 may have a health information field 1304 (e.g., a text field, a numeric field, a calendar field, a drop-down menu, etc.). In the example embodiment illustrated in FIG. 13, the health information field 1304 may be a numeric field used to enter blood glucose (e.g., in units of mg/dl). The health information box 1302 may also include a submit button 1306 used to commit the entered value in the health information field 1304 to a health information repository associated with the software application 602 (e.g., stored within the device 302 and/or stored within an associated server). In other embodiments, there may be more than one health information field (e.g., possibly for different types of health information, such as one health information field for blood glucose, one health information field for blood pressure, and one health information field for body weight). In some embodiments, in addition to or instead of requesting results of an at-home diagnostic test, the health information box 1302 may prompt a user (e.g., a corresponding patient) to perform a different health management task. For example, the health information box 1302 may prompt a user to perform a specific type of exercise, to eat a specific type/quantity of food, or to sleep for a specific number of hours.

At-home diagnostic tests may be prompted by the software application 602 based on a corresponding patient's disease state. For example, if a patient has type I diabetes the interval at which the patient performs and reports the results of an at-home blood glucose test may be different than if a patient has type II diabetes. The corresponding patient's disease state may be provided by a healthcare provider (e.g., a physician, a nurse, a hospital, an insurance provider, a pharmacy, etc.), by the corresponding patient, or by an approved third party (e.g., the spouse or parent of the corresponding patient). Further, the corresponding patient's disease state may be provided by a user of the software application 602 (e.g., a physician, a corresponding patient, or an approved third party) or retrieved from a health information repository (e.g., associated with the software application 602 or associated with a hospital).

Alternatively, based on the medications that the corresponding patient is taking (e.g., stored within a repository associated with the software application 602), a list of possible disease states may be generated, and a user of the software application 602 may choose from a list of the disease states based on one or more disease states actually exhibited by the corresponding patient. For example, if the patient is presently prescribed a medication typically associated with high blood pressure, the software application 602 may ask a user (e.g., the patient) if the patient has high blood pressure. If the user responds in the affirmative, then the high blood pressure disease state may be added to a list of disease states of the patient. This list may be used to prompt at-home diagnostic tests or provide reminders (e.g., reminder to visit a physician or refill a prescription) to a user of the software application 602 (e.g., the patient), as described above. Further, scheduled reminders and/or prompted at-home diagnostic tests may be adjusted over time based on changes in the patient's disease state(s) and/or rates of changes in the patient's disease state(s).

The health information box 1302 may be used to indicate information to a user of the device 302/software application 602 (e.g., to the corresponding patient) in addition to or instead of requesting results from an at-home diagnostic test (e.g., a blood glucose test or a body weighing). For example, the health information box 1302 could be used to remind a patient: to schedule an appointment (e.g., with a specific healthcare provider, such as a specific physician), to attend a previously scheduled appointment (e.g., with a specific healthcare provider, such as a specific physician), to pick up a medication (e.g., a prescription medication) from a specific pharmacy, to refill a medication (e.g., a prescription medication), to request authorization of a healthcare provider (e.g., a specific physician) to authorize a refill of a given medication (e.g., a given prescription medication), to attend a previously scheduled appointment to run laboratory tests (e.g., a previously scheduled appointment to have blood samples collected and blood tests run), etc.

In still other embodiments, rather than using a manual entry method for health information, an image may be captured to provide health information. For example, an image may be captured using a camera (e.g., a smartphone camera of the device 302) via the omnibus scanning region 802. Using image analysis (e.g., OCR), the captured image may be analyzed by a computing device to determine captured health information. For example, if the health information includes a blood glucose level for a patient, and the captured image is of a device used to measure blood glucose, a reading of the device (as captured in the image) may include units associated with blood glucose (e.g., mg/dl). These units may be read by the computing device using OCR/text recognition, for example. Thus, the computing device can determine what type of health information is contained in the captured image and can store the information in a corresponding health information repository (e.g., within the device 302 and/or a server).

Figure 14:
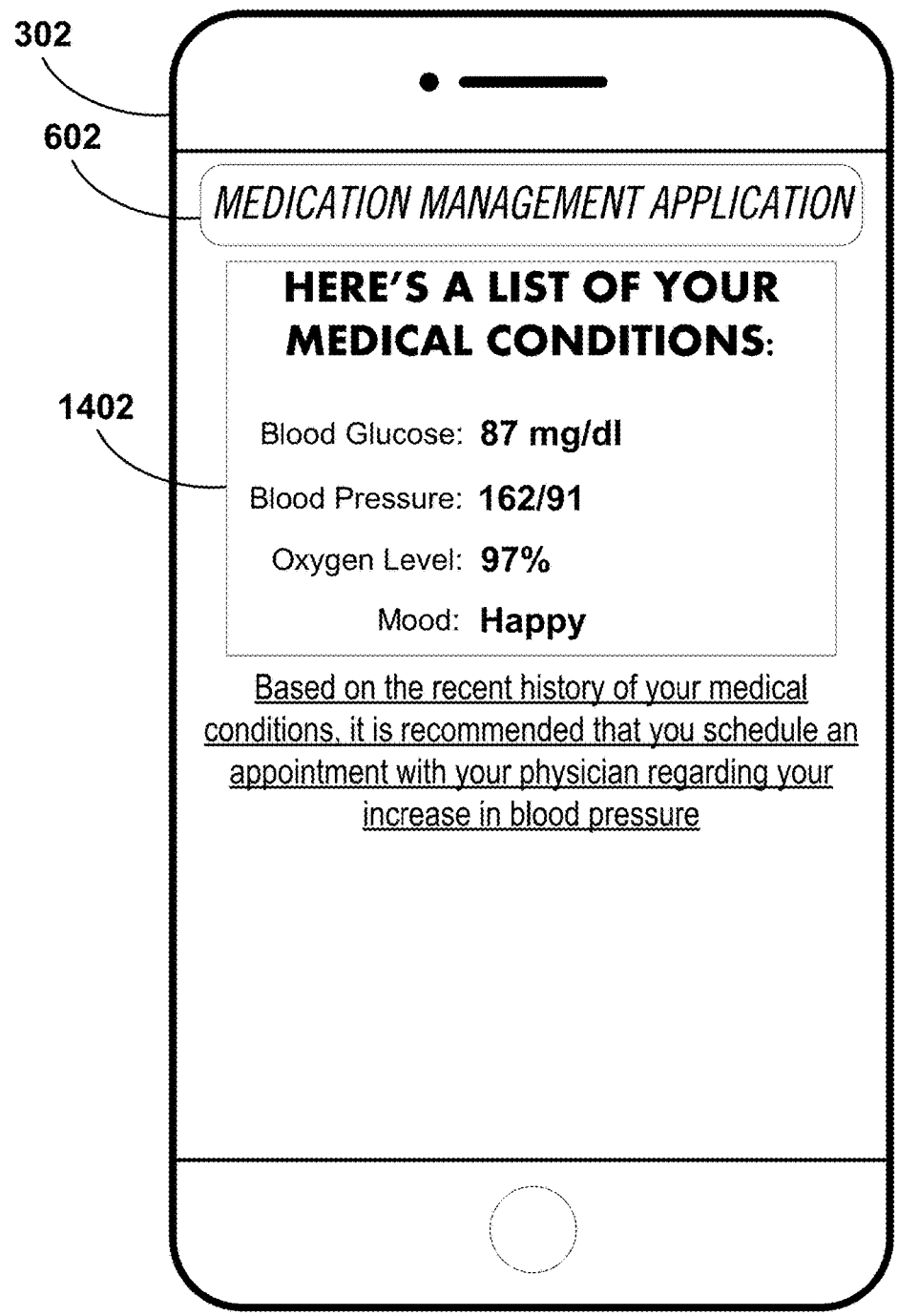
FIG. 14 is an illustration of a medication management application executed by a mobile computing device in accordance with at least one embodiment.

In some embodiments, a hybrid of the two above-described techniques may be used. For example, a user could provide a captured image along with a tag that indicates what type of health information is shown in the captured image. In this way, the computing device may select a specific type of image processing algorithm to determine what the health information is. For example, the computing device may select an OCR/text recognition algorithm if the captured health information is a scale reading of a body weight, but may instead select an edge-detection algorithm if the captured health information is a height of a patient based on a captured image of the patient and reference points (e.g., on a tape measurer or ruler also present in the captured image). FIG. 14 illustrates features of the software application 602, according to example embodiments. Similar to FIG. 13, as illustrated in FIG. 14, the software application 602 may include a health information box. The health information box in FIG. 14 may include a health information summary 1402. The health information summary 1402 may include a list of the most pertinent health information for a corresponding patient. The most pertinent health information may be selected by a user of the software application 602 (e.g., a patient or a healthcare provider), may be selected based on severity (e.g., the health information that poses the greatest present risk to a corresponding patient), or may be selected based on a disease state of a corresponding patient (e.g., if a patient has diabetes, blood glucose information will be included in the health information summary 1402). In addition to displaying the most pertinent health information for review in the health information summary 1402, the software application 602 may display any recommended health maintenance tasks. For example, as illustrated in FIG. 14, the software application 602 may recommend to a user (e.g., the patient) that the patient contact a physician based on some of the health information (e.g., based on high blood pressure).

In some embodiments, other information (e.g., other alerts/recommendations) can be displayed using the software application 602. For example, the software application 602 may display a suggested diet or workout regimen based on the corresponding patient's health information (e.g., "it is recommended that the patient reduce caloric intake to 2200 calories/day" or "it is recommended that the patient raise her heart rate to 130 bpm for at least 30 minutes three times a week"). Additionally or alternatively, the software application 602 can provide medication adherence advice (e.g., based on the adherence indicated by the corresponding patient), advice on how to report at-home diagnostic results (e.g., correct units to include in a text field within the software application 602 for at-home diagnostic test results), and/or advice on how their presently prescribed medication improves health outcomes (e.g., "did you know that 40% of patients who take metformin with 100% compliance for 3 months reduce their A1c by 1.1%, on average?"). Even further, the software application 602 may include instructional games and/or videos that could be displayed in order to assist the corresponding patient in achieving her healthcare goals or adhering to her medication/workout/diet regimens (e.g., as prescribed by one or more healthcare providers).

Figure 15A:
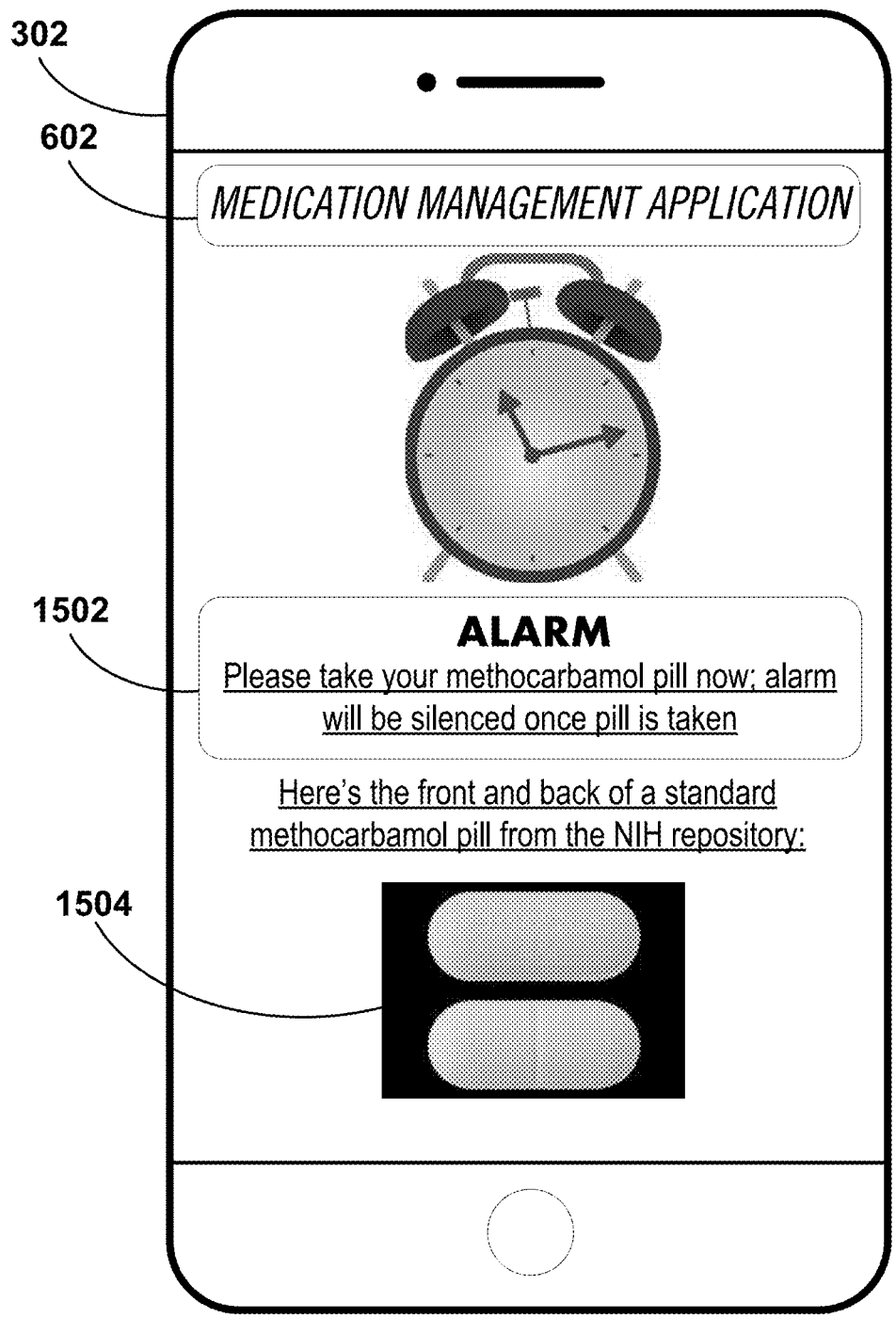
FIG. 15A is an illustration of a medication management application executed by a mobile computing device in accordance with at least one embodiment.

FIG. 15A illustrates features of the software application 602, according to example embodiments. When medication schedule(s) (e.g., a medication schedule previously generated by a computing device based on a captured image of a medication label) for a corresponding patient dictates that a medication is to be taken by the corresponding patient, an alarm 1502 may be sounded/displayed by the software application 602. The alarm 1502 may assist in reminding the corresponding patient to take the proper medication(s) in the proper dosage strength(s) at the proper time of day. As illustrated, the alarm 1502 may include a statement about which medication is presently to be taken by the corresponding patient (e.g., "please take your methocarbamol pill now," "please take 500 mg of ibuprofen now," "please take 100 mg of hydrocodone within the next half hour," "please take three of pill type X and two of pill type Y before breakfast," etc.). In some embodiments, the alarm 1502 may include braille instructions. Braille may also be used in conjunction with any other aspect of the embodiments described herein (e.g., braille may be used to prompt at-home diagnostic tasks, to display medication information, etc.).

In some embodiments, the alarm 1502 may be silenced once the patient or a user of the device 302 provides evidence and/or a confirmation that the medication has been taken in the appropriate amount. In other embodiments, the alarm 1502 may be silenced by a user of the device 302 independently of providing evidence/confirmation that the medication has been taken in the appropriate amount. In some embodiments, in addition to or instead of a reminder about taking a medication based on a medication schedule, the software application 602 may provide a reminder to perform a scheduled health maintenance task (e.g., perform a given diagnostic test or workout for a specific duration).

Also as illustrated, the software application 602 may display a reminder image 1504 to assist in the patient taking the appropriate medication and/or the appropriate dosage strength. For example, the reminder image 1504 may be an image of a pill (e.g., showing the shape, color, size, etc. of the pill) that corresponds to the scheduled medication. In some embodiments, the image of the pill may be taken from a government (e.g., NIH) repository or from a public repository associated with a pharmaceutical company (e.g., the pharmaceutical company that manufactures the corresponding medication). Additionally or alternatively, the image of the pill may be stored in a repository associated with the software application 602 (e.g., stored within the device 302 and/or within a server). In some embodiments, the repository of reminder medication images may include a flattened, gold standard image of the overall morphology of every pill from every manufacturer.

In addition to a reminder image 1504 that illustrates the medication, in some embodiments, instructional images, diagrams, videos, or audio instructions may accompany the alarm 1502. The instructional images, instructional diagrams, instructional videos, or audio instructions may describe to a user of the software application 602 (e.g., a patient or an approved third party) how to take the medication. For example, if the medication is an ointment, there may be an instructional image or instructional video showing where on the body and in what approximate quantity to apply the ointment. Alternatively, if the medication is an injectionable, there may be an instructional diagram or instructional video showing how to load an injection device with the injectionable and where on the body to inject the injectionable. Other example instructional images, instructional diagrams, instructional videos, or audio instructions are also possible.

Reminder images 1504, instructional images, instructional diagrams, instructional videos, or audio instructions may be provided by the software application 602 as popup notifications, text messages, emails, in-app notifications, push notifications, etc. Further, the software application 602 may request and/or require confirmation that a user (e.g., the patient or an approved third party) has received the corresponding reminder image 1504, instructional image, instructional diagram, instructional video, or audio instructions. In example embodiments where the device 302 includes a smart speaker (e.g., a smart speaker with a virtual assistant, such as SIRI, ALEXA, GOOGLE ASSISTANT, BIXBY, or CORTANA), the user may provide such a confirmation using voice affirmation.

In some embodiments, the alarm 1502 and/or the reminder image 1504 may have associated indicators (e.g., shape(s), color(s), number(s), symbol(s), sound(s), light(s), etc.). The associated indicators may correspond to a medication that is to be taken by the patient. For example, a corresponding shape, color, number, symbol, etc. may be printed on a medication container corresponding to the appropriate medication or on the appropriate medication itself (e.g., a pill may be the corresponding color), and the same corresponding shape, color, number, symbol, etc. may be displayed in the reminder image 1504. In this way, a user of the device 302 may have an additional technique by which to determine the appropriate medication.

Figure 15B:
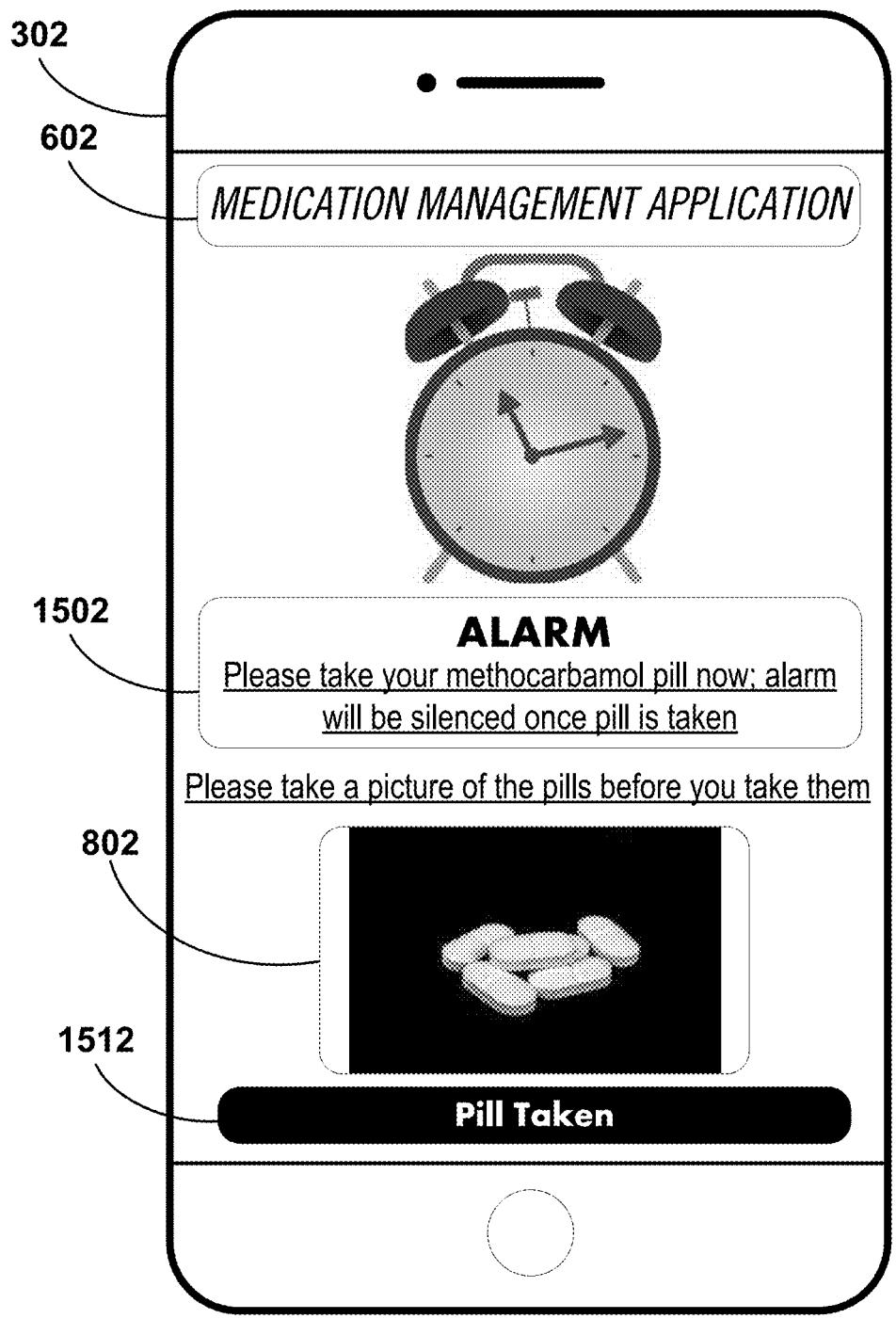
FIG. 15B is an illustration of a medication management application executed by a mobile computing device in accordance with at least one embodiment.

FIG. 15B illustrates features of the software application 602, according to example embodiments. In some embodiments, the software application 602 may display an alarm silence button 1512 when displaying the alarm 1502. As illustrated, the alarm silence button 1512 may be a confirmation that the corresponding medication has been taken. In some embodiments, the alarm silence button 1512 may snooze or dismiss the alarm 1502, regardless if the corresponding has been taken by the patient. In some embodiments, both types of alarm silence buttons previously described (e.g., a confirmation button and a snooze/dismiss button) may be displayed simultaneously.

Also as illustrated in FIG. 15B, an image of the medication that the patient is about to take may be captured (e.g., using a camera) via the omnibus scanning region 802. In some embodiments, in addition to or instead of capturing an image of the physical medication (e.g., the pills themselves), an image of a corresponding medication container and/or a corresponding medication label may be captured. Further, in some embodiments, video or audio may be captured (e.g., a patient could speak into a microphone to say what kind of medication they will be taking and in what quantity or the patient could video record themselves taking a medication).

The captured image may then be analyzed (e.g., by the device 302 and/or by a server associated with the software application 602) to ensure the patient is taken the proper medication (e.g., the medication corresponding to the alarm 1502) in the proper dosage. The captured image may be analyzed before the patient takes the medication in the captured image or after the patient takes the medication in the captured image, in various embodiments. If the proper medication and/or proper dosage is not captured in the image of the medication, the device 302 may provide a warning (e.g., by displaying a warning on the device 302 and/or sounding a warning using speakers of the device 302). Such warnings are shown and described with reference to FIG. 15C below.

In other embodiments, the alarm 1502 may be silenced using alternative methods. For example, a medication container (e.g., pill bottle) may include a transmitter that emits electromagnetic signals (e.g., near-field communication (NFC) signals, radio-frequency identification (RFID) signals, signals based on Institute of Electrical and Electronics Engineers (IEEE) 802.11 standards (WIFI signals), signals based on IEEE 802.15.4 standards (Zigbee signals), or BLUETOOTH signals). Such signals may be encrypted, in some embodiments. The device 302 may include or may be communicatively coupled to a receiver that receives the electromagnetic signals emitted by the transmitter when the receiver is positioned sufficiently proximate to the transmitter. Once the receiver detects the electromagnetic signals emitted by the transmitter, the alarm 1502 may be silenced.

In some embodiments, the alarm 1502 may include a virtual assistant from an associated smart speaker (e.g., SIRI, ALEXA, GOOGLE ASSISTANT, BIXBY, CORTANA, etc.) or from the device 302 providing an audio reminder to a patient reminding the patient to take the corresponding medication in a corresponding quantity. The audio reminder to the patient may be repeated by the virtual assistant at predetermined intervals (e.g., every 15 seconds, every 30 seconds, every minute, every 2 minutes, every 5 minutes, every 10 minutes, every 15 minutes, every 20 minutes, every 30 minutes, every hour, etc.) until silenced by a spoken command received by the virtual assistant (e.g., via a microphone attached to or integrated with the smart speaker). Further, in some embodiments, the alarm 1502 may only be silenced by the user for whom the notification is intended (e.g., by the patient or by an approved healthcare provider of the patient). This may be achieved using a speaker recognition (i.e., voice recognition) algorithm executed by a processor onboard the smart speaker or within a server associated with the software application 602, for example.

Figure 15C:
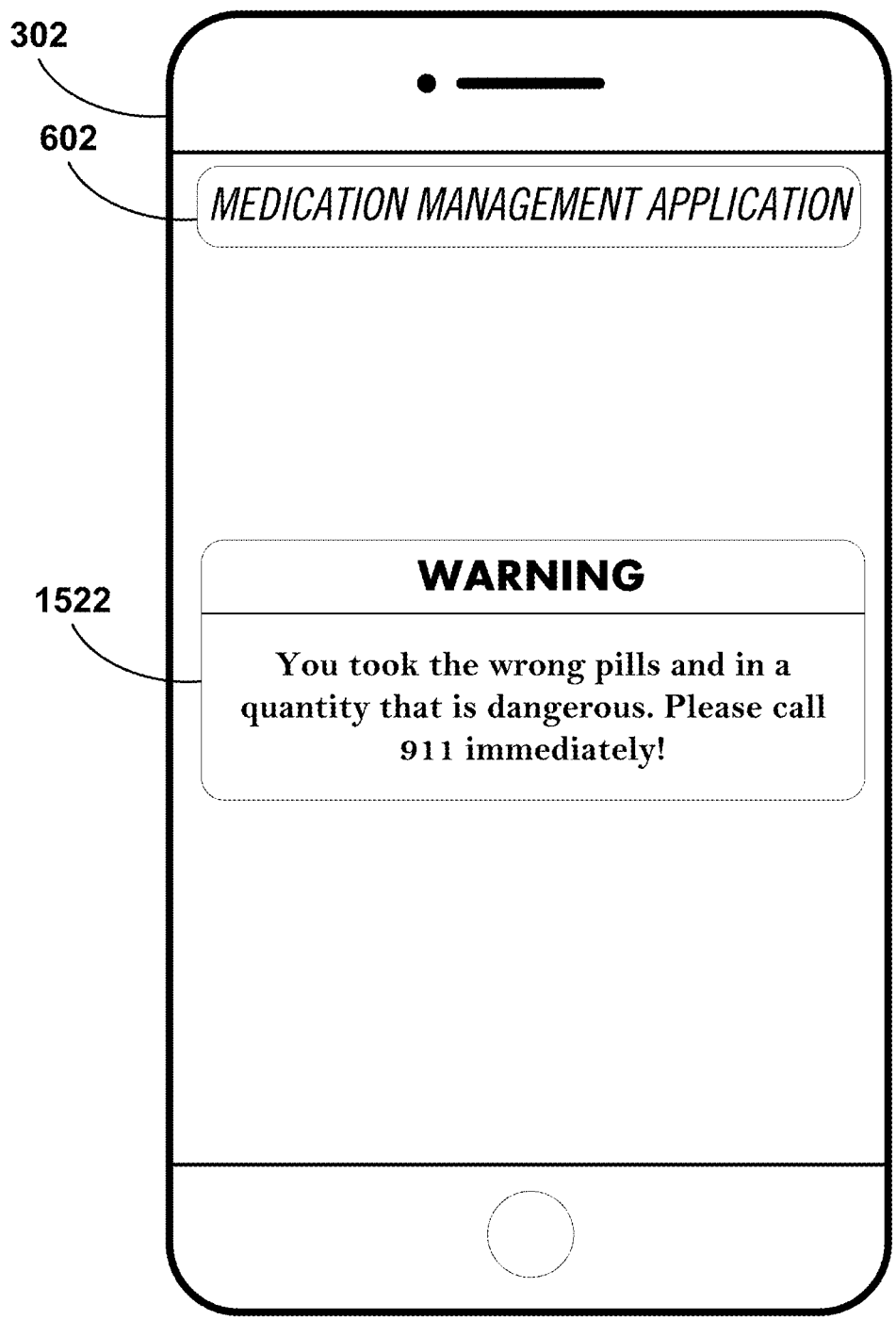
FIG. 15C is an illustration of a medication management application executed by a mobile computing device in accordance with at least one embodiment.

FIG. 15C illustrates features of the software application 602, according to example embodiments. As described above, the software application 602 may display a warning 1522 when a patient has taken or is about to take the wrong medication or an inappropriate dosage (e.g., an overdose). The warning 1522 may be triggered based on an image of the medication that the patient is about to take that is captured in response to an alarm 1502. In some embodiments, the warning 1522 may include a sound and/or a video.

The warning 1522 may provide a user of the device 302 (e.g., a patient or a healthcare provider) with instructions. For example, the warning 1522 may state "please refrain from taking the medication pictured" or, as illustrated, "You took the wrong pills and in a quantity that is dangerous. Please call 911 immediately!" In other embodiments, a phone number of the nearest poison control center may be listed and/or immediately dialed by the device 302. In some embodiments, the warning 1522 may provide a recommendation that the patient take the appropriate medication and/or dosage in the future (e.g., if a patient takes a single ibuprofen pill, but it is recommended that the patient take two ibuprofen pills, the warning 1522 may state "You have been instructed by a physician to take two ibuprofen pills every morning for pain, rather than one. In the future, take two ibuprofen pills instead."). Similarly, the warning 1522 may provide an instruction to a physician (e.g., if the physician were a user of the device 302) to provide remedial instructions to the corresponding patient regarding the corresponding medication.

Figure 16:
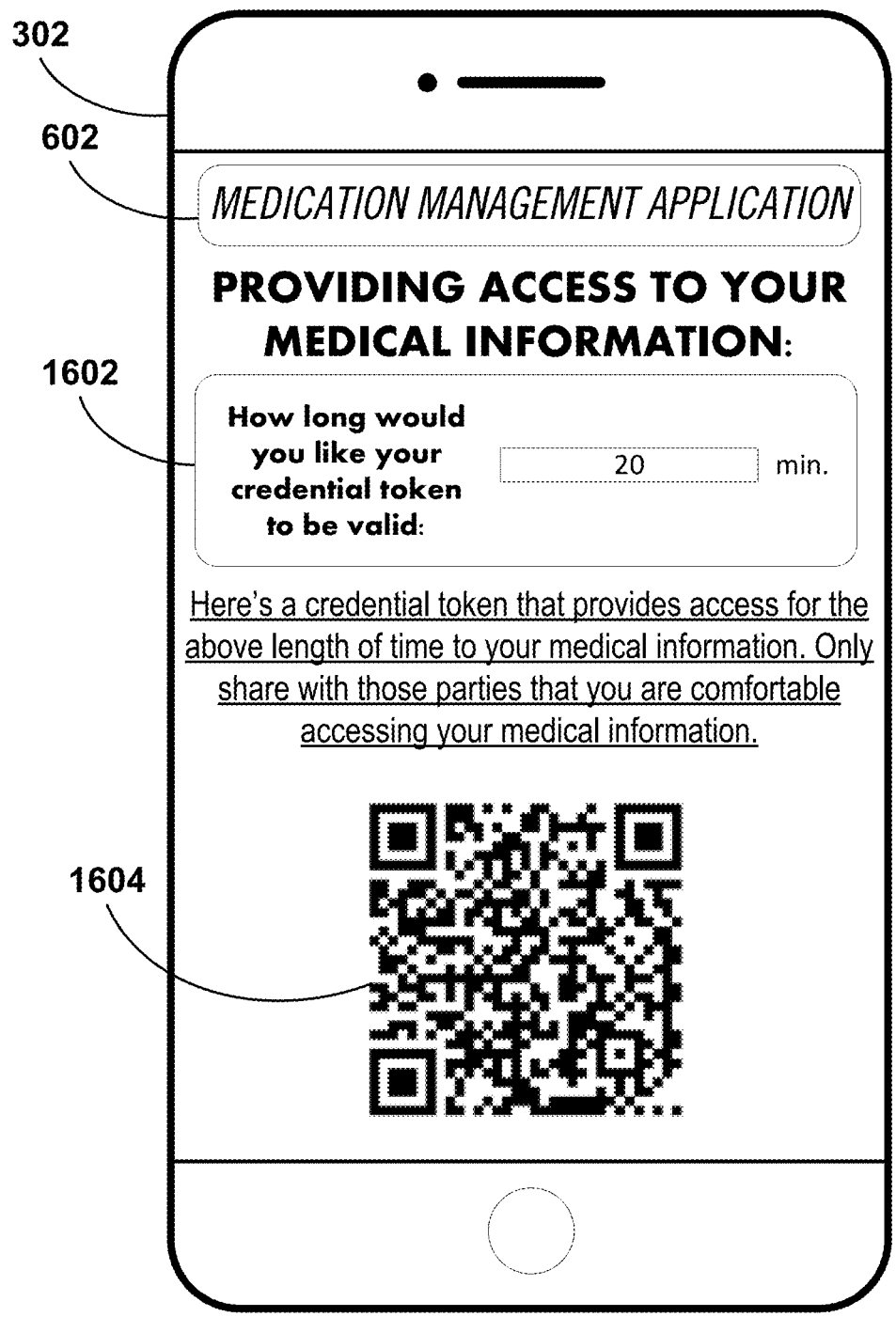
FIG. 16 is an illustration of a medication management application executed by a mobile computing device in accordance with at least one embodiment.

FIG. 16 illustrates features of the software application 602, according to example embodiments. The software application 602 may display a credential token request dialog box 1602 used in generating a credential token and a generated credential token 1604. The generated credential token 1604 may provide access to a corresponding patient's private health information (e.g., medication schedules, treatment regimen, disease states, name of medication(s) being taken, dosage amount of medication(s), dosage frequency of medication(s), medication adherence log that indicates when a patient has actually taken certain medications). This information may be provided to a pharmacist, physician, or other trusted third party (e.g., family member), for example.

As illustrated, the credential token request dialog box 1602 may capture information that is used to generate a credential token. For example, the credential token request dialog box 1602 may capture information regarding which user(s) (e.g., based on corresponding username) can utilize the generated credential token 1604. Additionally or alternatively, the credential token request dialog box 1602 may capture information regarding the duration for which the generated credential token 1604 will be valid after initial use (e.g., 10 minutes, 20 minutes, 30 minutes, 1 hour, 2 hours, 3 hours, 5 hours, 24 hours, 1 week, 1 month, etc.) or information regarding an expiration date before which the generated credential token 1604 must be used. Hence, the credential token request dialog box 1602 may include one or more entry fields (e.g., text fields, numeric fields, calendar fields, drop down menus, etc.).

The generated credential token 1604 may be transmitted from the device 302 (e.g., the patient's device) to a different device (e.g., a device of a family member or a physician). For example, the generated credential token 1604 may be an image (e.g., .png, .jpeg, .bmp, etc.) or a password (e.g., a string of text or an integer) that may be emailed or sent within a text message to a different device. As illustrated, the generated credential token 1604 may be a generated QR code. Alternatively, the generated credential token 1604 may be a generated barcode. Once the image or the password is received by another device, that device may submit the image or the password to a server associated with the software application 602 via an instance of the software application 602 on that device. The software application 602 may then provide access to the device that submitted the generated credential token 1604: until access is manually revoked by the device 302 that initially produced the generated credential token 1604 or for a predetermined time as set by the user whose device initially produced the generated credential token 1604. Providing access to the health information of the patient may include allowing the device that submitted the generated credential token 1604 to access a server associated with the software application 602 that stores health information for the patient. Additionally or alternatively, providing access to the health information of the patient may include a server associated with the software application 602 transmitting a copy of the health information of the patient (e.g., in the form of one or more electronic files having extension types .pdf, .doc, .jpeg, .png, .bmp, .xls, .csv, .txt, etc.) to the device that submitted the generated credential token 1604.

Figure 17:
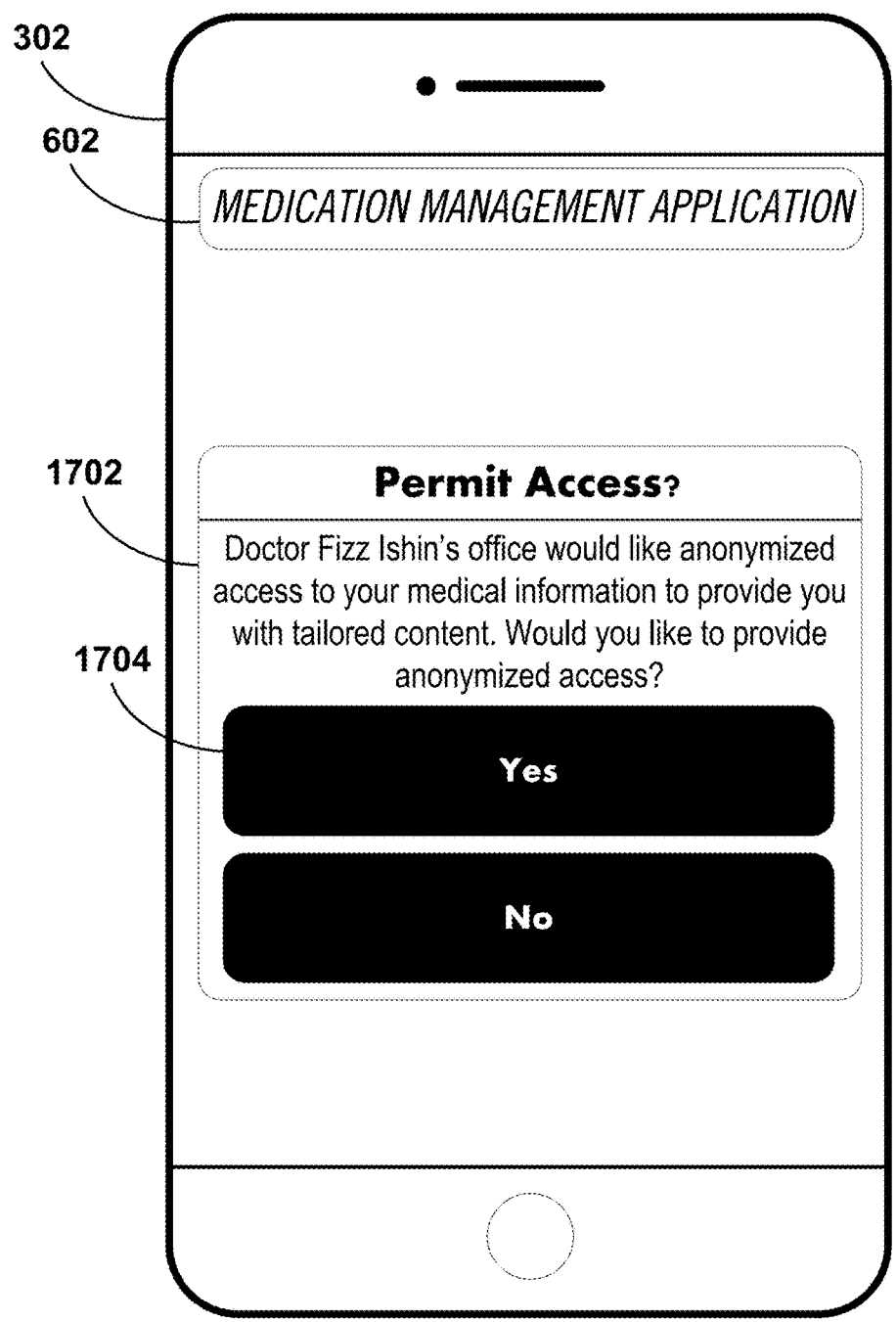
FIG. 17 is an illustration of a medication management application executed by a mobile computing device in accordance with at least one embodiment.

FIG. 17 illustrates features of the software application 602, according to example embodiments. In some embodiments, one or more devices may use the software application 602 to provide tailored content (e.g., advertisements for specific medications based on a patient's disease state or health conditions) to one or more other devices associated with the software application 602. Such tailored content may be produced using health information from a plurality of devices.

In some embodiments, a device providing tailored content may broadcast a request 1702 to each other device within a predetermined proximity of the device providing tailored content. For example, a device in a physician's office or a waiting room of an emergency care facility may broadcast a request 1702 to other devices. The request 1702 may request access to health information about the corresponding patient of each device/each instance of the software application 602. Using response buttons 1704, a user of the device 302 (e.g., the corresponding patient) may select whether to provide access to such health information to the device in the physician's office or the waiting room of the emergency care facility. If the user selects not to provide access to the health information of the corresponding patient, the request 1702 may be removed from the display of the device 302. If the user selects to provide access to the health information, the health information of the corresponding patient may be transmitted to the device providing the tailored content.

Transmitting the health information of the corresponding patient in such a way may include transmitting a copy of the health information of the corresponding patient (e.g., in the form of one or more electronic files having extension types .pdf, .doc, .jpeg, .png, .bmp, .xls, .csv, .txt, etc.) to the device providing the tailored content and/or transmitting a credential token (e.g., similar to the generated credential token 1604 illustrated in FIG. 16) to the device providing the tailored content (e.g., to grant access to health information about the patient stored within a server associated with the software application 602). The health information provided may be anonymized in one or more ways. For example, the health information may not contain corresponding patient identification information (e.g., the patient name, the patient address, the patient social security number, the patient ID number, etc. may be stripped from the health information and/or redacted within the health information). Further, access to the health information may be revoked once the device 302 associated with the corresponding patient is no longer within the predetermined proximity of the device providing the tailored content or after a predetermined length of time.

Based on the health information from one or more devices, the device providing the tailored content may then provide targeted content (e.g., advertisements or promotions) to one or more patients within the predetermined proximity of the device providing the tailored content. For example, if 50% of the patients within a physician's office provide health information that indicates they have diabetes, an advertisement for diabetes medication may be sent to each device in the predetermined proximity or sent to each device that provided health information (e.g., via a push notification, a popup notification, a text message, an email, an in-app notification, a banner advertisement on a webpage, etc.). Additionally or alternatively, a video advertisement for a diabetes medication may play on a television present in the physician's office or an audio advertisement for diabetes medication may play on a speaker (e.g., over the radio) within the physician's office. Other types of targeted content are also possible. Further, other methods for providing targeted content are also possible.

Figure 18:
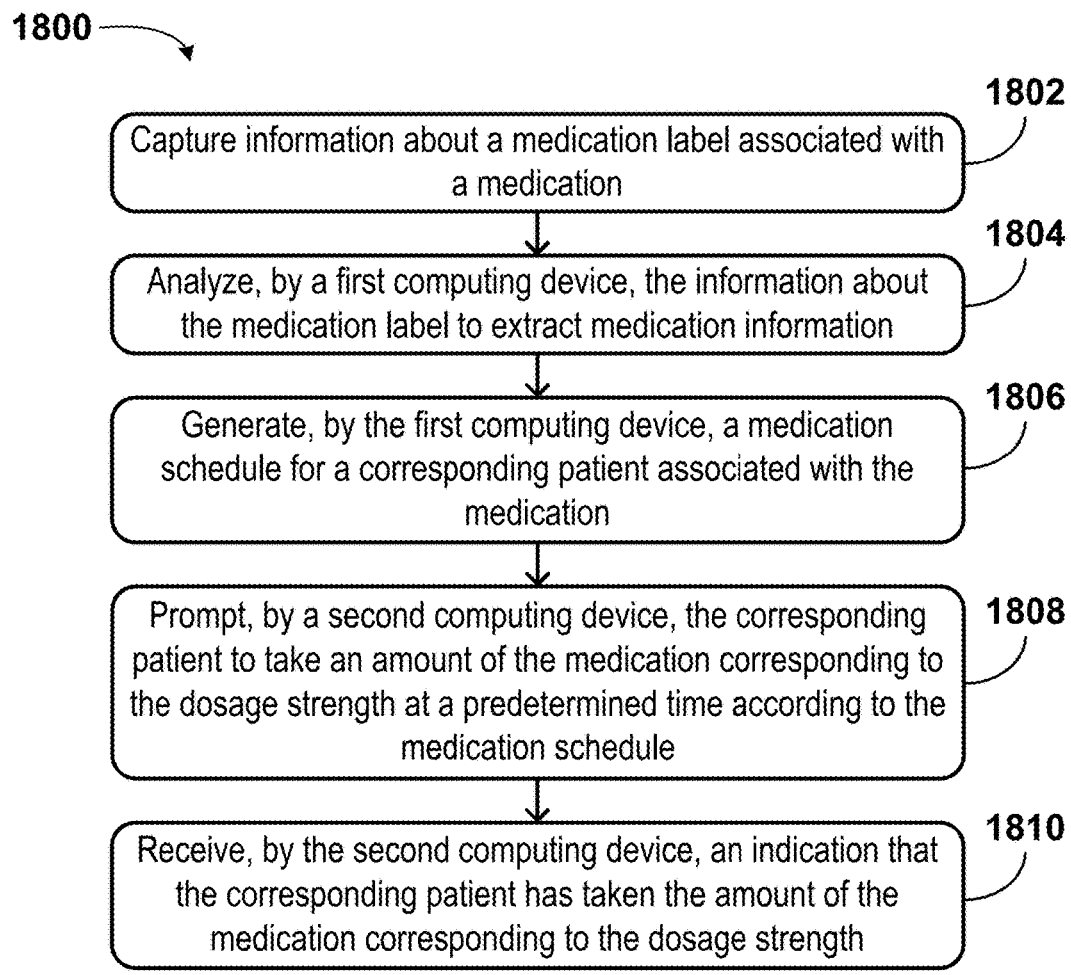
FIG. 18. is a flow chart illustrating a method in accordance with at least one embodiment.

FIG. 18 is a flow chart illustrating a method 1800.

At block 1802, the method 1800 may include capturing information about a medication label associated with a medication.

At block 1804, the method 1800 may include analyzing, by a first computing device, the information about the medication label to extract medication information.

At block 1806, the method 1800 may include generating, by the first computing device, a medication schedule for a corresponding patient associated with the medication. The medication schedule may include a dosage strength and dosage frequency.

At block 1808, the method 1800 may include prompting, by a second computing device, the corresponding patient to take an amount of the medication corresponding to the dosage strength at a predetermined time according to the medication schedule.

At block 1810, the method 1800 may include receiving, by the second computing device, an indication that the corresponding patient has taken the amount of the medication corresponding to the dosage strength.

In some embodiments of the method 1800, the medication information may include a name of a corresponding pharmacy, an address of a corresponding pharmacy, a phone number of a corresponding pharmacy, a name of a corresponding pharmacist, a name of a prescribing physician, a name of the corresponding patient, initials of the corresponding patient, a date of birth of the corresponding patient, a patient identification (ID) number of the corresponding patient, an address of the corresponding patient, a date on which a corresponding prescription was filled, a serial number of a corresponding prescription, directions for prescribed use of the medication, dosage information, a proprietary name of a corresponding drug, a generic name of a corresponding drug, an expiration date of the medication, a drug dose strength of the medication, or an initial quantity of pills in a corresponding container.

In some embodiments of the method 1800, block 1802 may include capturing, by a camera, an image of the medication label. Block 1802 may also include transmitting, by the camera, the image of the medication label to the first computing device.

In some embodiments of the method 1800, block 1804 may include performing, by the first computing device, optical character recognition (OCR) on the image of the medication label. Block 1804 may also include performing, by the first computing device, image analysis on the image of the medication label to read a barcode or a QUICK-RESPONSE (QR) code of the medication label.

In some embodiments of the method 1800, the dosage strength or dosage frequency may be based on the medication information.

In some embodiments, the method 1800 may include prompting, by the second computing device, the corresponding patient to complete a health management task. The method 1800 may also include receiving, by the second computing device, an indication that the corresponding patient has completed the health management task. The health management task may include performing an exercise, performing an at-home diagnostic test, or visiting a physician. In such embodiments, block 1810 may include receiving, by the second computing device, results of the at-home diagnostic test. Block 1810 may also include storing, within the second computing device or the first computing device, the results of the at-home diagnostic test.

In some embodiments, the method 1800 may include storing, within the first computing device, at least one of the medication schedule, the dosage strength, the dosage frequency, or the indication that the corresponding patient has taken the amount of the medication corresponding to the dosage strength. The method 1800 may also include presenting, to a physician treating the corresponding patient, the stored medication schedule, stored dosage strength, stored dosage frequency, or stored indication that the corresponding patient has taken the amount of the medication corresponding to the dosage strength.

In some embodiments, the method 1800 may include storing, within the first computing device, at least one of a name of the medication, the medication schedule, the dosage strength, the dosage frequency, or the indication that the corresponding patient has taken the amount of the medication corresponding to the dosage strength. The method 1800 may also include transmitting, by the second computing device, a credential token to a third computing device, wherein the credential token provides access privileges to an approved party for a predetermined length of time to the stored name of the medication, stored medication schedule, stored dosage strength, stored dosage frequency, or stored indication that the corresponding patient has taken the amount of the medication corresponding to the dosage strength. Further, the method 1800 may include providing, by the third computing device to the first computing device, the credential token. In addition, the method 1800 may include providing, to the third computing device by the first computing device, access to the stored name of the medication, stored medication schedule, stored dosage strength, stored dosage frequency, or stored indication that the corresponding patient has taken the amount of the medication corresponding to the dosage strength. Still further, the method 1800 may include revoking, after the predetermined length of time, the access privileges to the stored name of the medication, stored medication schedule, stored dosage strength, stored dosage frequency, or stored indication that the corresponding patient has taken the amount of the medication corresponding to the dosage strength.

In some embodiments, the method 1800 may include determining, by the first computing device based on the indication that the corresponding patient has taken the amount of the medication corresponding to the dosage strength, whether an appropriate medication was taken by the corresponding patient. The method 1800 may also include determining, by the first computing device based on the indication that the corresponding patient has taken the amount of the medication corresponding to the dosage strength, whether an appropriate amount of medication was taken by the corresponding patient. Further, the method 1800 may include determining, by the first computing device based on the indication that the corresponding patient has taken the amount of the medication corresponding to the dosage strength, whether the medication was taken within an appropriate time window based on the predetermined time. In such embodiments, the method 1800 may include providing, by the second computing device, an alert if: the appropriate medication was not taken by the corresponding patient, the appropriate amount of the medication was not taken by the corresponding patient, or the medication was not taken within the appropriate time window based on the predetermined time.

In some embodiments, the method 1800 may include revising, by the first computing device, the medication schedule based on a change in health or symptoms of the corresponding patient.

In some embodiments of the method 1800, block 1808 may include displaying, by the second computing device, an image of the medication; displaying, by the second computing device, an image of the dosage strength; displaying, by the second computing device, an instructional image regarding how to take the medication; providing, by the second computing device, audio instructions regarding how to take the medication; providing, by the second computing device, video instructions regarding how to take the medication; providing, by the second computing device, a text-message or email reminder regarding the medication; or providing, by the second computing device, a popup notification regarding the medication. In such embodiments, the image of the medication is a stock photo of a drug obtained from an image repository of a government agency or pharmaceutical corporation.

In some embodiments of the method 1800, the indication that the corresponding patient has taken the amount of the medication corresponding to the dosage strength includes a captured image of a medication taken by the corresponding patient.

In some embodiments of the method 1800, block 1808 may include activating, by the second computing device, an alarm. In such embodiments, the method 1800 may also include silencing, by the second computing device upon receiving the indication that the corresponding patient has taken the amount of the medication corresponding to the dosage strength, the alarm. Further, in such embodiments, block 1810 may include receiving, by the second computing device, the indication that the corresponding patient has taken the amount of the medication corresponding to the dosage strength may include interacting a pill container with a pill-container detection device.

In some embodiments, the method 1800 may include receiving, by the second computing device, context about a time at which the medication was taken by the corresponding patient. The method 1800 may also include storing, within the first computing device or the second computing device, the context about the time at which the medication was taken by the corresponding patient.

In some embodiments of the method 1800, the dosage strength may include a drug dosage strength in mg or a drug dosage amount in number of pills.

In some embodiments of the method 1800, the dosage strength or dosage frequency is based on health information about the corresponding patient stored within the first computing device, the second computing device, or some other computing device.

In some embodiments, the method 1800 may include determining an amount of the medication remaining in a medication container. The method 1800 may also include storing, within the first computing device, the amount of medication remaining in the medication container. In such embodiments, determining the amount of medication remaining in the medication container may include weighing all pills remaining in the medication container and dividing by a predetermined mass of each pill; pouring out pills remaining in the medication container, capturing an image of the pills, and performing image processing on the captured image to count a number of pills; or subtracting the amount of medication corresponding to the dosage strength from a previously determined amount of remaining medication to establish the amount of the medication remaining in the medication container.

In some embodiments, the method 1800 may include broadcasting, by a third computing device within a waiting room of an emergency care facility or a physician's office, a beacon requesting access to medical information about the corresponding patient. The method 1800 may also include granting, by the second computing device for a predetermined length of time, access to the medical information about the corresponding patient. Further, the method 1800 may include broadcasting, by the third computing device within the waiting room of the emergency care facility or the physician's office, targeted content that is tailored based on the medical information about the corresponding patient.

In some embodiments of the method 1800, block 1802 may include capturing, by a camera, a first image of the medication label. Block 1802 may also include transmitting, by the camera, the first image of the medication label to the first computing device. Further, block 1802 may include determining, by the first computing device, that the first image is obscured or blurry. In addition, block 1802 may include prompting, by the second computing device, the corresponding patient to capture an additional image of the medication label. Still further, block 1802 may include capturing, by the camera, a second image of the medication label. Even further, block 1802 may include transmitting, by the camera, the second image of the medication label to the first computing device. In such embodiments, the method 1800 may also include determining, by the first device, that the second image is obscured or blurry. The method 1800 may further include prompting, by the second computing device, the corresponding patient to manually enter the information about the medication label associated with the medication.

In some embodiments, the method 1800 may also include capturing information about an additional medication label associated with an additional medication. Further, the method 1800 also includes analyzing, by the computing device, the information about the additional medication label to extract additional medication information. In addition, the method 1800 may include generating, by the first computing device, an additional medication schedule for the corresponding patient. The additional medication schedule may include an additional dosage strength and an additional dosage frequency corresponding to the additional medication. In such embodiments, block 1806 may include determining if any potential adverse drug interactions exist between the medication and the additional medication. Block 1806 may also include staggering, if a potential adverse drug interaction does exist, predetermined times to take the medication according to the medication schedule with respect to predetermined times to take the additional medication according to the additional medication schedule.

In some embodiments of the method 1800, the first computing device may be a cloud computing device or a server computing device.

In some embodiments of the method 1800, the second computing device is a mobile computing device, a tablet computing device, a wearable computing device, a laptop computing device, a desktop computing device, a computing device associated with a smart speaker, or a computing device embedded within a household appliance.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed:

1. A method comprising:
   capturing information about a medication label associated with a medication;
   analyzing, by a first computing device, the information about the medication label to extract medication information;
   generating, by the first computing device, a medication schedule for a corresponding patient associated with the medication, wherein the medication schedule comprises a dosage strength and dosage frequency;
   prompting, by a second computing device, the corresponding patient to take an amount of the medication corresponding to the dosage strength at a predetermined time according to the medication schedule; and
   receiving, by the second computing device, an indication that the corresponding patient has taken the amount of the medication corresponding to the dosage strength.

2. The method of claim 1, wherein the medication information comprises a name of a corresponding pharmacy, an address of a corresponding pharmacy, a phone number of a corresponding pharmacy, a name of a corresponding pharmacist, a name of a prescribing physician, a name of the corresponding patient, initials of the corresponding patient, a date of birth of the corresponding patient, a patient identification (ID) number of the corresponding patient, an address of the corresponding patient, a date on which a corresponding prescription was filled, a serial number of a corresponding prescription, directions for prescribed use of the medication, dosage information, a proprietary name of a corresponding drug, a generic name of a corresponding drug, an expiration date of the medication, a drug dose strength of the medication, or an initial quantity of pills in a corresponding container.

3. The method of claim 1, wherein capturing the information about the medication label comprises:
   capturing, by a camera, an image of the medication label; and
   transmitting, by the camera, the image of the medication label to the first computing device.

4. The method of claim 3, wherein analyzing the information about the medication label to extract medication information comprises:
   performing, by the first computing device, optical character recognition (OCR) on the image of the medication label; or
   performing, by the first computing device, image analysis on the image of the medication label to read a barcode or a QUICK-RESPONSE (QR) code of the medication label.

5. The method of claim 1, wherein the dosage strength or dosage frequency is based on the medication information.

6. The method of claim 1, further comprising:
   prompting, by the second computing device, the corresponding patient to complete a health management task; and
   receiving, by the second computing device, an indication that the corresponding patient has completed the health management task, wherein the health management task comprises performing an exercise, performing an at-home diagnostic test, or visiting a physician.

7. The method of claim 6, wherein receiving the indication that the corresponding patient has completed the health management task comprises:
   receiving, by the second computing device, results of the at-home diagnostic test; and
   storing, within the second computing device or the first computing device, the results of the at-home diagnostic test.

8. The method of claim 1, further comprising:
   storing, within the first computing device, at least one of the medication schedule, the dosage strength, the dosage frequency, or the indication that the corresponding patient has taken the amount of the medication corresponding to the dosage strength; and
   presenting, to a physician treating the corresponding patient, the stored medication schedule, stored dosage strength, stored dosage frequency, or stored indication that the corresponding patient has taken the amount of the medication corresponding to the dosage strength.

9. The method of claim 1, further comprising:
storing, within the first computing device, at least one of a name of the medication, the medication schedule, the dosage strength, the dosage frequency, or the indication that the corresponding patient has taken the amount of the medication corresponding to the dosage strength;
transmitting, by the second computing device, a credential token to a third computing device, wherein the credential token provides access privileges to an approved party for a predetermined length of time to the stored name of the medication, stored medication schedule, stored dosage strength, stored dosage frequency, or stored indication that the corresponding patient has taken the amount of the medication corresponding to the dosage strength;
providing, by the third computing device to the first computing device, the credential token;
providing, to the third computing device by the first computing device, access to the stored name of the medication, stored medication schedule, stored dosage strength, stored dosage frequency, or stored indication that the corresponding patient has taken the amount of the medication corresponding to the dosage strength; and
revoking, after the predetermined length of time, the access privileges to the stored name of the medication, stored medication schedule, stored dosage strength, stored dosage frequency, or stored indication that the corresponding patient has taken the amount of the medication corresponding to the dosage strength.

10. The method of claim 1, further comprising:
determining, by the first computing device based on the indication that the corresponding patient has taken the amount of the medication corresponding to the dosage strength, whether an appropriate medication was taken by the corresponding patient;
determining, by the first computing device based on the indication that the corresponding patient has taken the amount of the medication corresponding to the dosage strength, whether an appropriate amount of medication was taken by the corresponding patient; or
determining, by the first computing device based on the indication that the corresponding patient has taken the amount of the medication corresponding to the dosage strength, whether the medication was taken within an appropriate time window based on the predetermined time.

11. The method of claim 10, further comprising providing, by the second computing device, an alert if:
the appropriate medication was not taken by the corresponding patient;
the appropriate amount of the medication was not taken by the corresponding patient; or
the medication was not taken within the appropriate time window based on the predetermined time.

12. The method of claim 1, further comprising revising, by the first computing device, the medication schedule based on a change in health or symptoms of the corresponding patient.

13. The method of claim 1, wherein prompting, by the second computing device, comprises:
displaying, by the second computing device, an image of the medication;
displaying, by the second computing device, an image of the dosage strength;
displaying, by the second computing device, an instructional image regarding how to take the medication;
providing, by the second computing device, audio instructions regarding how to take the medication;
providing, by the second computing device, video instructions regarding how to take the medication;
providing, by the second computing device, a text-message or email reminder regarding the medication; or
providing, by the second computing device, a popup notification regarding the medication.

14. The method of claim 13, wherein the image of the medication is a stock photo of a drug obtained from an image repository of a government agency or pharmaceutical corporation.

15. The method of claim 1, wherein the indication that the corresponding patient has taken the amount of the medication corresponding to the dosage strength comprises a captured image of a medication taken by the corresponding patient.

16. The method of claim 1,
wherein prompting, by the second computing device, the corresponding patient to take the amount of the medication corresponding to the dosage strength comprises activating, by the second computing device, an alarm, and
wherein the method further comprises silencing, by the second computing device upon receiving the indication that the corresponding patient has taken the amount of the medication corresponding to the dosage strength, the alarm.

17. The method of claim 16, wherein receiving, by the second computing device, the indication that the corresponding patient has taken the amount of the medication corresponding to the dosage strength comprises interacting a pill container with a pill-container detection device.

18. The method of claim 1, further comprising:
receiving, by the second computing device, context about a time at which the medication was taken by the corresponding patient; and
storing, within the first computing device or the second computing device, the context about the time at which the medication was taken by the corresponding patient.

19. The method of claim 1, wherein the dosage strength comprises a drug dosage strength in mg or a drug dosage amount in number of pills.

20. The method of claim 1, wherein the dosage strength or dosage frequency is based on health information about the corresponding patient stored within the first computing device, the second computing device, or some other computing device.

21. The method of claim 1, further comprising:
determining an amount of the medication remaining in a medication container; and
storing, within the first computing device, the amount of medication remaining in the medication container.

22. The method of claim 21, wherein determining the amount of the medication remaining in the medication container comprises:
weighing all pills remaining in the medication container and dividing by a predetermined mass of each pill;
pouring out pills remaining in the medication container, capturing an image of the pills, and performing image processing on the captured image to count a number of pills; or
subtracting the amount of medication corresponding to the dosage strength from a previously determined amount of remaining medication to establish the amount of the medication remaining in the medication container.

23. The method of claim 1, further comprising:
broadcasting, by a third computing device within a waiting room of an emergency care facility or a physician's office, a beacon requesting access to medical information about the corresponding patient;
granting, by the second computing device for a predetermined length of time, access to the medical information about the corresponding patient; and
broadcasting, by the third computing device within the waiting room of the emergency care facility or the physician's office, targeted content that is tailored based on the medical information about the corresponding patient.

24. The method of claim 1, wherein capturing information about the medication label associated with the medication comprises:
capturing, by a camera, a first image of the medication label;
transmitting, by the camera, the first image of the medication label to the first computing device;
determining, by the first computing device, that the first image is obscured or blurry;
prompting, by the second computing device, the corresponding patient to capture an additional image of the medication label;
capturing, by the camera, a second image of the medication label; and
transmitting, by the camera, the second image of the medication label to the first computing device.

25. The method of claim 24, further comprising:
determining, by the first computing device, that the second image is obscured or blurry; and
prompting, by the second computing device, the corresponding patient to manually enter the information about the medication label associated with the medication.

26. The method of claim 1, further comprising:
capturing information about an additional medication label associated with an additional medication;
analyzing, by the first computing device, the information about the additional medication label to extract additional medication information; and
generating, by the first computing device, an additional medication schedule for the corresponding patient, wherein the additional medication schedule comprises an additional dosage strength and an additional dosage frequency corresponding to the additional medication.

27. The method of claim 26, wherein generating the additional medication schedule comprises:
determining if any potential adverse drug interactions exist between the medication and the additional medication; and
staggering, if a potential adverse drug interaction does exist, predetermined times to take the medication according to the medication schedule with respect to predetermined times to take the additional medication according to the additional medication schedule.

28. The method of claim 1, wherein the first computing device is a server computing device.

29. The method of claim 1, wherein the second computing device is a mobile computing device, a tablet computing device, a wearable computing device, a laptop computing device, a desktop computing device, a computing device associated with a smart speaker, or a computing device embedded within a household appliance.

30. A mobile computing device configured to:
capture information about a medication label associated with a medication;
analyze the information about the medication label to extract medication information;
generate a medication schedule for a corresponding patient associated with the medication, wherein the medication schedule comprises a dosage strength and dosage frequency;
prompt the corresponding patient to take an amount of the medication corresponding to the dosage strength at a predetermined time according to the medication schedule; and
receive an indication that the corresponding patient has taken the amount of the medication corresponding to the dosage strength.

31. A non-transitory, computer-readable medium having instructions stored thereon that, when executed by a processor, perform a method comprising:
receiving information, from a computing device, about a medication label associated with a medication;
analyzing the information about the medication label to extract medication information;
generating a medication schedule for a corresponding patient associated with the medication, wherein the medication schedule comprises a dosage strength and dosage frequency;
transmitting, to the computing device, the medication schedule for the corresponding patient; and
receiving, from the computing device, an indication that the corresponding patient has taken an amount of the medication corresponding to the dosage strength, wherein the indication that the corresponding patient has taken the amount of the medication corresponding to the dosage strength was received by the computing device in response to the computing device prompting the corresponding patient to take the amount of the medication corresponding to the dosage strength at a predetermined time according to the medication schedule.

* * * * *